United States Patent
Khorram et al.

(10) Patent No.: US 10,517,842 B2
(45) Date of Patent: Dec. 31, 2019

(54) METHODS OF MODULATING MIRNA LEVELS AND COMPOSITIONS FOR USE IN THE SAME

(71) Applicant: Los Angeles Biomedical Research Institute at Harbor-UCLA Medical Center, Torrance, CA (US)

(72) Inventors: Omid Khorram, Rolling Hills, CA (US); Tsai-Der Chuang, Inglewood, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 15/921,380

(22) Filed: Mar. 14, 2018

(65) Prior Publication Data
US 2018/0263941 A1 Sep. 20, 2018

Related U.S. Application Data

(60) Provisional application No. 62/471,744, filed on Mar. 15, 2017.

(51) Int. Cl.
*A61K 31/196* (2006.01)
*C12Q 1/6883* (2018.01)
*A61P 35/00* (2006.01)

(52) U.S. Cl.
CPC ............ *A61K 31/196* (2013.01); *A61P 35/00* (2018.01); *C12Q 1/6883* (2013.01); *C12Q 2600/178* (2013.01)

(58) Field of Classification Search
CPC .............................. A61K 31/19; A61K 31/196
See application file for complete search history.

(56) References Cited

U.S. PATENT DOCUMENTS 7,799,782 B2 * 9/2010 Munson ............... C07D 231/56
514/234.5

OTHER PUBLICATIONS

Chuang et al. Reproductive Science, 2016, 23(1): 65A.*
Hu et al., The Journal of Biological Chemistry, 2013, 288(32): 22972-84 (abstract).*
Nakatani et al., Journal of American Colleage of Cardiology, 2013, 61(5):582-588 (abstract).*
Shime et al., Journal of Clinical Endocrinology and Metabolism, 2002, 87(12): 5610-5617.*
McVicker et al, Front Pharmacol, 2017, 8:318 (abstract).*
Chuang et al., Tranilast Inhibits Genes Functionally Involved in Cell Proliferation, Fibrosis, and Epigenetic Regulation and Epigenetically Induces miR-29c Expression in Leiomyoma Cells, Reprod Sci. Sep. 2017;24(9):1253-1263, Abstract Only.
Chuang et al., Mechanisms underlying aberrant expression of miR-29c in uterine leiomyoma, Fertil Steril. Jan. 2016;105(1):236-45.
Chuang et al., The regulatory function of miR-200c on inflammatory and cell-cycle associated genes in SK-LMS-1, a leiomyosarcoma cell line, Reprod Sci. May 2015;22(5):563-71, Abstract Only.
Chuang et al., miR-29c induction contributes to downregulation of vascular extracellular matrix proteins by glucocorticoids, Am J Physiol Cell Physiol. Jul. 15, 2015;309(2):C117-25.
Chuang et al., miR-200c regulates IL8 expression by targeting IKBKB: a potential mediator of inflammation in leiomyoma pathogenesis, PLoS One. Apr. 22, 2014;9(4):e95370.

* cited by examiner

*Primary Examiner* — Rei Tsang Shiao
(74) *Attorney, Agent, or Firm* — Bret E. Field; Bozicevic, Field & Francis LLP

(57) ABSTRACT

Methods of modulating a miRNA level, such as a miR-29c and/or miR-200c level, in a cell are provided. Aspects of the methods include contacting the cell with an anti-fibrotic miRNA modulating active agent, such as a tranilast active agent. Also provided are compositions for use in practicing the methods. The methods and compositions find use in a variety of applications, including the treatment of fibrotic disorders, such as a uterine leiomyoma.

13 Claims, 15 Drawing Sheets

Specification includes a Sequence Listing.

FIG. 1A
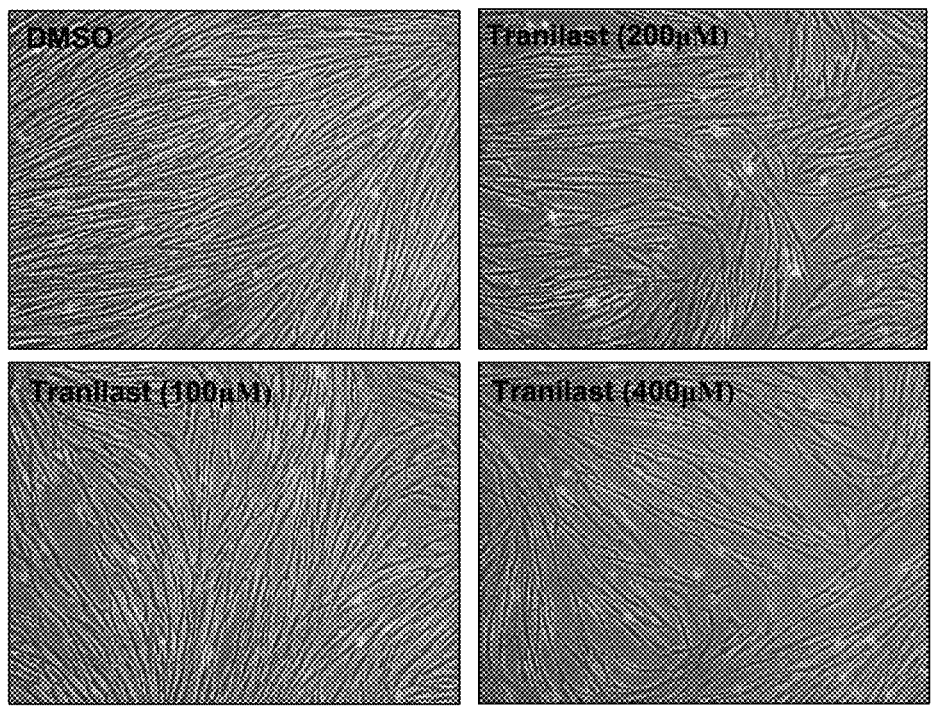
FIG. 1B MTT
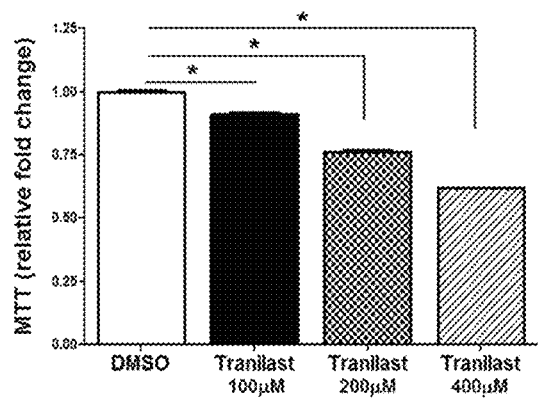
FIG. 1C Caspase 3/7
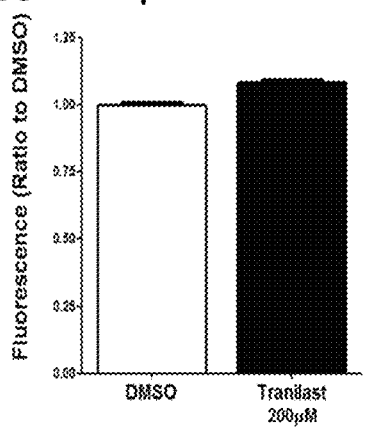

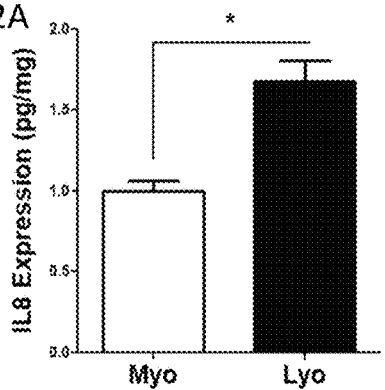
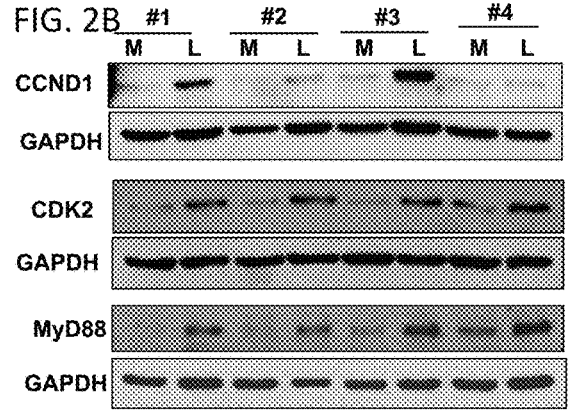
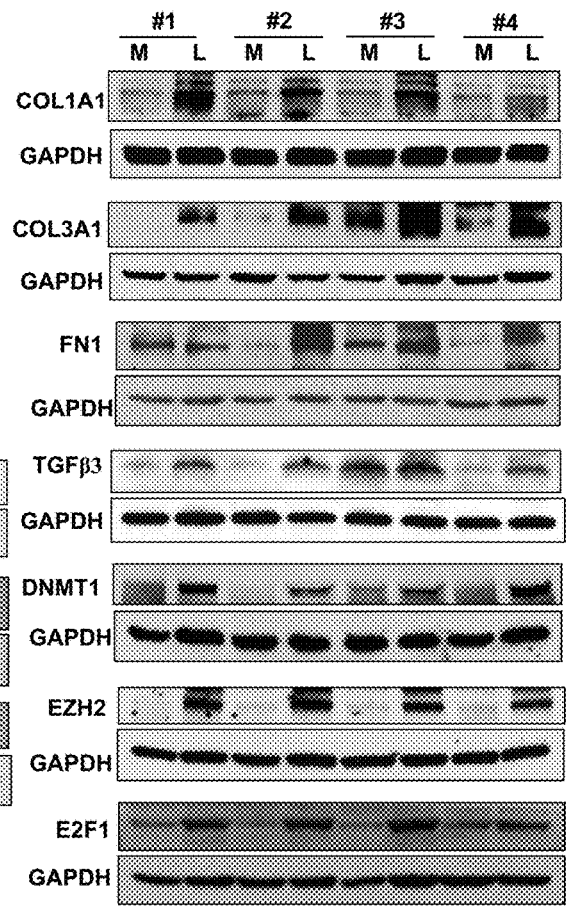
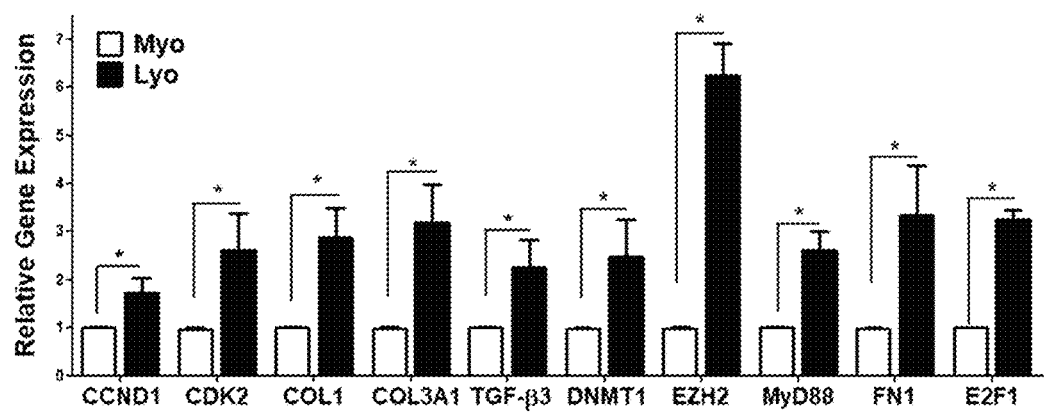
FIG. 2A  
FIG. 2B  
FIG. 2C

FIG. 3A
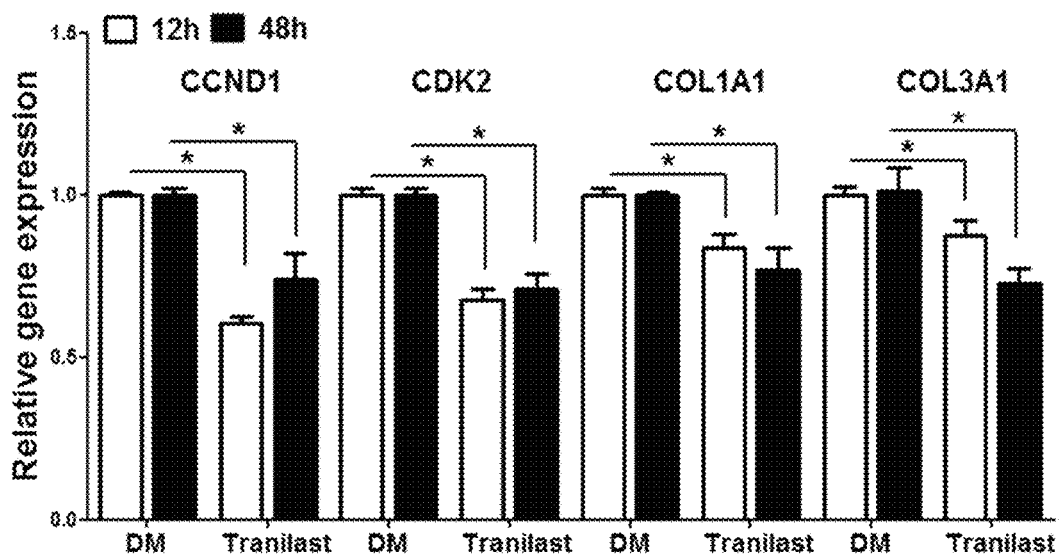
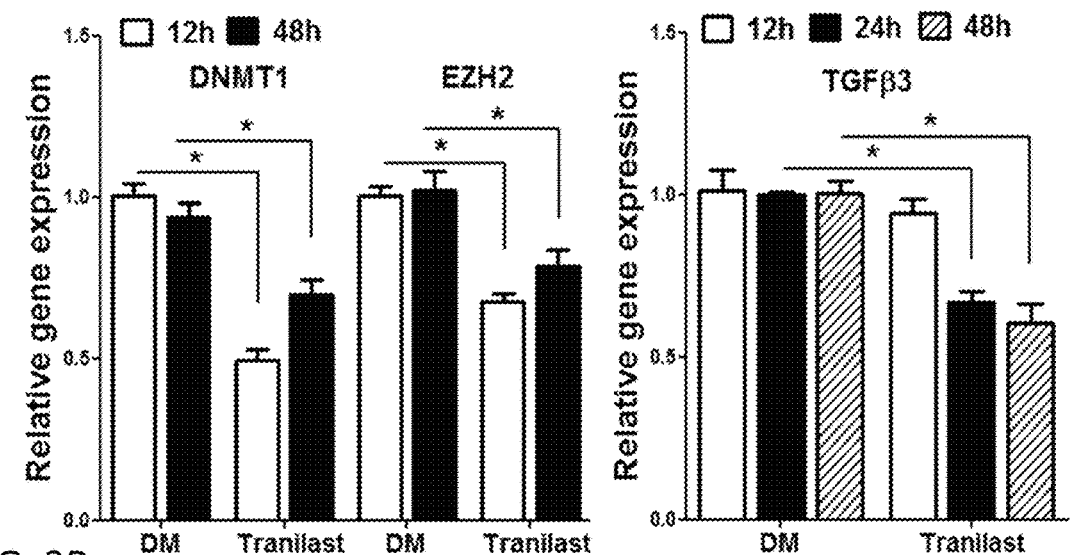
FIG. 3B
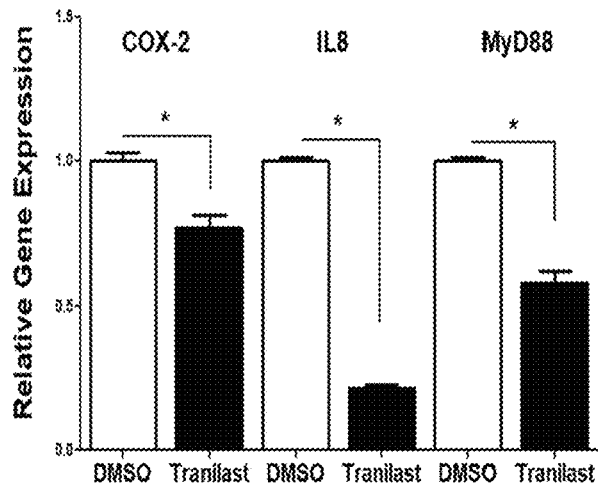

FIG. 5A Cellular miR-29c and miR-200c    FIG. 5B Secreted miR-29c and miR-200c
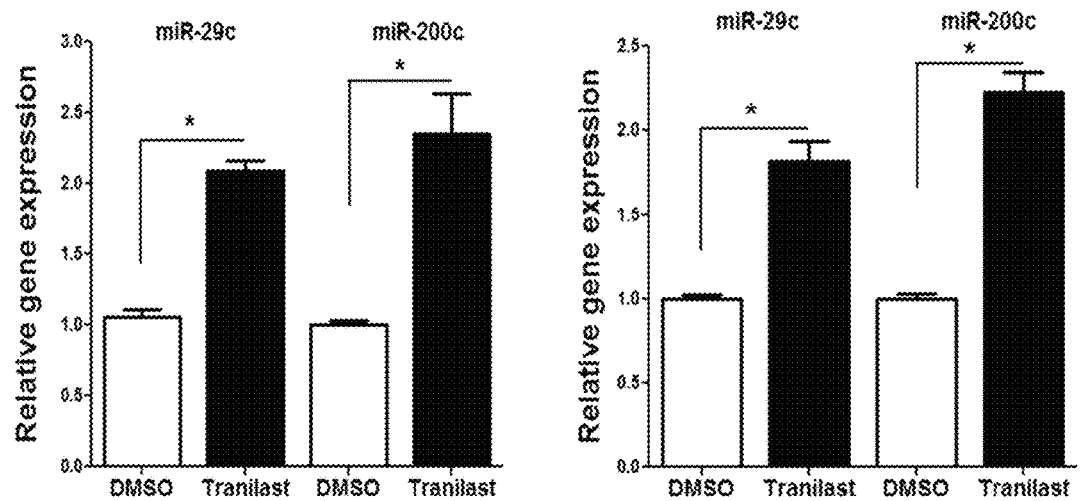
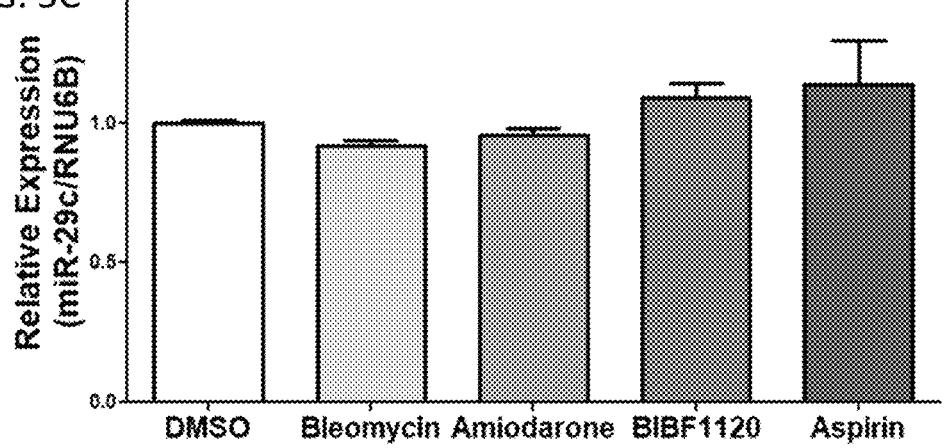
FIG. 5C

FIG. 7A

COL3A1
Position 242-248 of Col3A1 3' UTR

5' ...UUCAAAAUGUCUCAAUGGUGCUA...
         ||| | | ||
3'    AUUGGCUAAAGUUUACCACGAU miR-29c

Position 682-688 of Col3A1 3' UTR

5' ...UAAAGACGCAUGUUAUGGUGCUA...
         |||| | ||
3'    AUUGGCUAAAGUUUACCACGAU miR-29c

CDK2
Position 426-432 of human CDK2 3' UTR

5' ...UAGCGGGGGCUAAGUUGGUGCUU...
              | ||| | | |
3'    AUUGGCUAAAGUUUACCACGAU miR-29c

COL1A1
Position 880-886 of Col1A1 3' UTR

5'   ...CCAUUUUAUACCAAAGGUGCUAC...
         | | ||       ||||| |
3' AUUGGCUAAAGUUUA-------CCACGAU miR-29c

Position 922-928 of Col1A1 3' UTR

5' ...UGGGGAGGGAAUCACUGGUGCUA...
                      |||||||
3'    AUUGGCUAAAGUUUACCACGAU miR-29c

Position 1055-1061 of Col1A1 3' UTR

5'   ...GUGAAUUUUUCUAAAGGUGCUAU...
         ||| |        ||||| |
3'  AUUGGCUAAAGUUUA----CCACGAU miR-29c

TGFβ3
Position 885-891 of human TGFβ3 3' UTR

5'   ...GUGUUCCUGGAAGCAGGUGCUAC...
                       ||| || |
3'     AUUGGCUAAAGUUUACCACGAU miR-29c

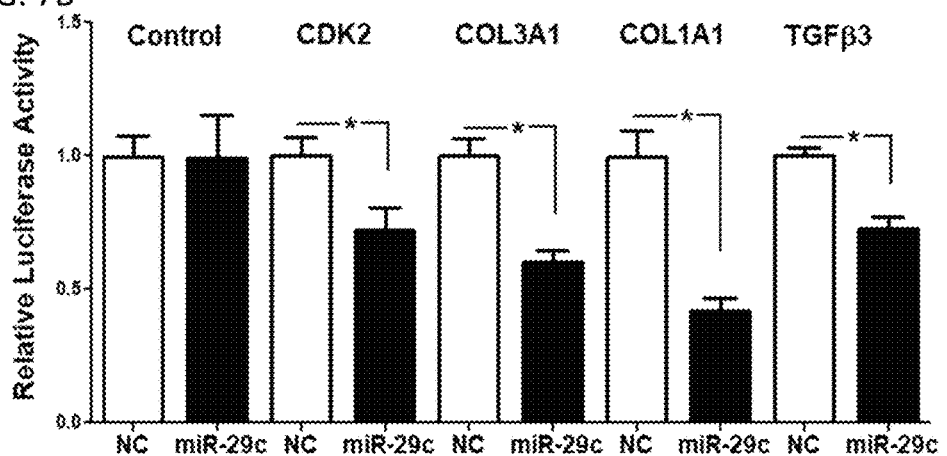

CDK2
Position 194-200 of human CDK2 3' UTR

5'  ...AAUGAAAGGAAGUUUCAGUAUUA...
         | | || ||  |
3'    AGGUAGUAAUGGGCCGUCAUAAU miR-200c

MyD88
Position 1227-1233 of human MyD88 3' UTR

5'  ...AAGGACCCAAUGUACCAGUAUUU...
                        | | | | | | |
3' AGGUAGUAAUGGGCCGUCAUAAU miR-200c

IL8
Position 206-212 of human IL8 3' UTR

5'  ...CAUACUUAUAUGUAAAGUAUUAU...
         | | |           | | | | | |
3' AGGUAGUAAUGGGCCG---UCAUAAU miR-200c

IL8
Position 543-549 of human IL8 3' UTR

5'  ...UUUCUAAGUGGAAAAAGUAUUAG...
                        | | | | | |
3' AGGUAGUAAUGGGCCGUCAUAAU miR-200c

FN1
Position 244-250 of human FN1 3' UTR

5' ...GUAUUCAAUACCGCUCAGUAUUU...
        | | | |     | | | | | | |
3'    AGGUAGUAAUGGGCCGUCAUAAU miR-200c

FN1
Position 530-536 of human FN1 3' UTR

5' ...UUUAUCAAUUUUUCCCAGUAUUU...
                       | | | | | | |
3' AGGUAGUAAUGGGCCGUCAUAAU miR-200c

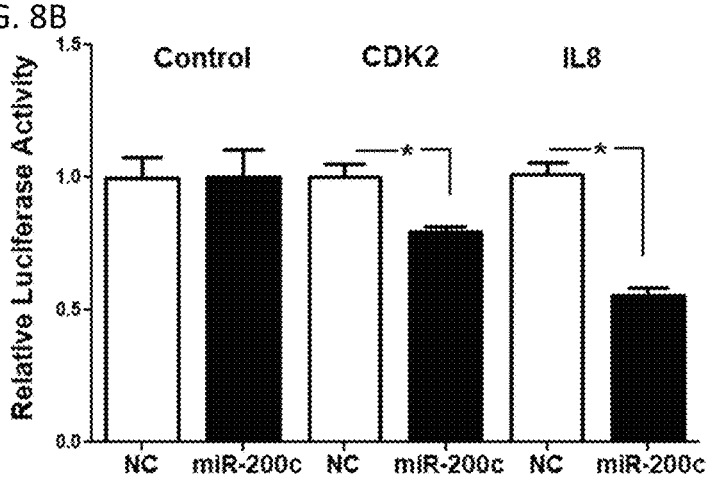

FIG. 8B

METHODS OF MODULATING MIRNA LEVELS AND COMPOSITIONS FOR USE IN THE SAME

CROSS-REFERENCE TO RELATED APPLICATION

Pursuant to 35 U.S.C. § 119 (e), this application claims priority to the filing date of the U.S. Provisional Patent Application Ser. No. 62/471,744, filed Mar. 15, 2017; the disclosure of which application is herein incorporated by reference.

INTRODUCTION

A microRNA (interchangeably referred to both in the art and herein as a miRNA or miR) is a non-coding RNA molecule, often between 20 and 30 nucleotides in length. MicroRNAs are endogenously expressed by eukaryotes and have been recognized to be key factors in the regulation of gene expression. MicroRNAs are originally expressed as a primary microRNA transcript, and processed to their mature form as a single stranded small RNA molecule.

MicroRNAs (miRNAs) are emerging as central players in regulating the expression of protein-coding RNA. This regulatory action of miRNAs occurs by binding to the complementary sequences (miRNA recognition element) located in the 3' untranslated region (UTR) of the mRNA, using a short sequence of approximately 2-8 nucleotides (the seed region) at the 5' end of the miRNA. Based on this property, one miRNA can have more than one target mRNA. The interaction of miRNA with 3' UTR of the mRNA alters the translation process and protein synthesis, resulting in changes in complex cellular regulatory networks.

SUMMARY

Methods of modulating a miRNA level, such as a miR-29c and/or miR-200c level, in a cell are provided. Aspects of the methods include contacting the cell with an anti-fibrotic miRNA modulating active agent, such as a tranilast active agent. Also provided are compositions for use in practicing the methods. The methods and compositions find use in a variety of applications, including the treatment of fibrotic disorders, such as a uterine leiomyoma.

BRIEF DESCRIPTION OF THE FIGURES

FIG. 1A: Photomicrographs of LSMC treated with Tranilast (100 to 400 µM) for 48 hrs. FIG. 1B: The rate of LSMC proliferation as determined by MTT assay following Tranilast treatment (100 to 400 µM) for 48 hrs. *: $P<0.05$ in this and subsequent figures. FIG. 1C: The influence of Tranilast (200 µM) on caspase 3/7 activity in LSMC after 48 hrs of treatment. The results are presented as mean±SEM of at least three independent experiments in six replicates using LSMC isolated from 3 patients.

FIG. 2A: IL8 levels determined by ELISA of tissue extracts from 11 leiomyoma (Lyo) and paired myometrium (Myo) from the untreated group. FIG. 2B: Representative immunoblots for cyclin D1 (CCND1), CDK2, COL1A1, COL3A1, TGF-β3, DNMT1, EZH2, MyD88, fibronectin (FN1) and E2F1 in paired myometrium (M) and leiomyoma (L). FIG. 2C: Bar graph shows relative band densities (N=12) in myometrium (MYO) and leiomyoma (LYO). The results are presented as mean±SEM. *: $p<0.05$.

FIG. 3A: mRNA expression of CCND1, CDK2, COL1, COL3A1, TGF-β3, DNMT1, EZH2, COX-2, IL8 and MyD88 in LSMC treated with Tranilast (200 µM) or DMSO (DM) as control for 12 h to 48 h. FIG. 3B: Treatment with Tranilast (200 µM) for 24 h in LSMC. The results are presented as mean±SEM of at least three independent experiments using LSMC isolated from 3 patients. *: $p<0.05$.

FIGS. 5A & 5B show the levels of miR-29c of miR-200c in (FIG. 5A) cellular and (FIG. 5B) medium after treatment of LSMC with Tranilast (200 µM) for 48 hours. FIG. 5C: The effect of anti-inflammatory agent (Aspirin; 10 mM), anti-fibrotic agent (BIBF 1120; 0.5 µM) and agents induced fibrosis (bleomycin, 10 µg/ml and amiodarone, 1 µM) on miR-29c level after 48 hours. The results are presented as mean±SEM of at least three independent experiments using LSMC isolated from 3 patients. *: $p<0.05$.

FIG. 7A: Complementary sequences between miR-29c and 3'UTR of COL3A1, COL1A1, CDK2 and TGFβ3. FIG. 7B: The relative luciferase activity in isolated leiomyoma smooth muscle cells (LSMC) co-transfected with *Renilla* and firefly luciferase reporter carrying a 3'UTR fragment of COL3A1, COL1A1, CDK2 and TGFβ3, pre-miR-29c or control oligonucleotides (NC) for 48 hrs. The relative luciferase activity is presented as the ratio of Firefly:*Renilla* as compared to NC which was independently set as 1. The results are presented as mean±SEM of at least three independent experiments with p values (*$P<0.05$) indicated by corresponding lines.

FIG. 8A: Complementary sequences between miR-200c and 3'UTR of CDK2, IL8, MyD88 and FN1. FIG. 8B: The relative luciferase activity in LSMC (for CDK2) and SK-LMS-1 (for IL8) co-transfected with *Renilla* and firefly luciferase reporter carrying a 3'UTR fragment of CDK2, IL8, pre-miR-200c or control oligonucleotides (NC) for 48 hrs. The relative luciferase activity is presented as the ratio of Firefly:*Renilla* as compared to NC which was independently set as 1. The results are presented as mean±SEM of at least three independent experiments with p values (*$P<0.05$) indicated by corresponding lines.

DEFINITIONS

Figure 4:
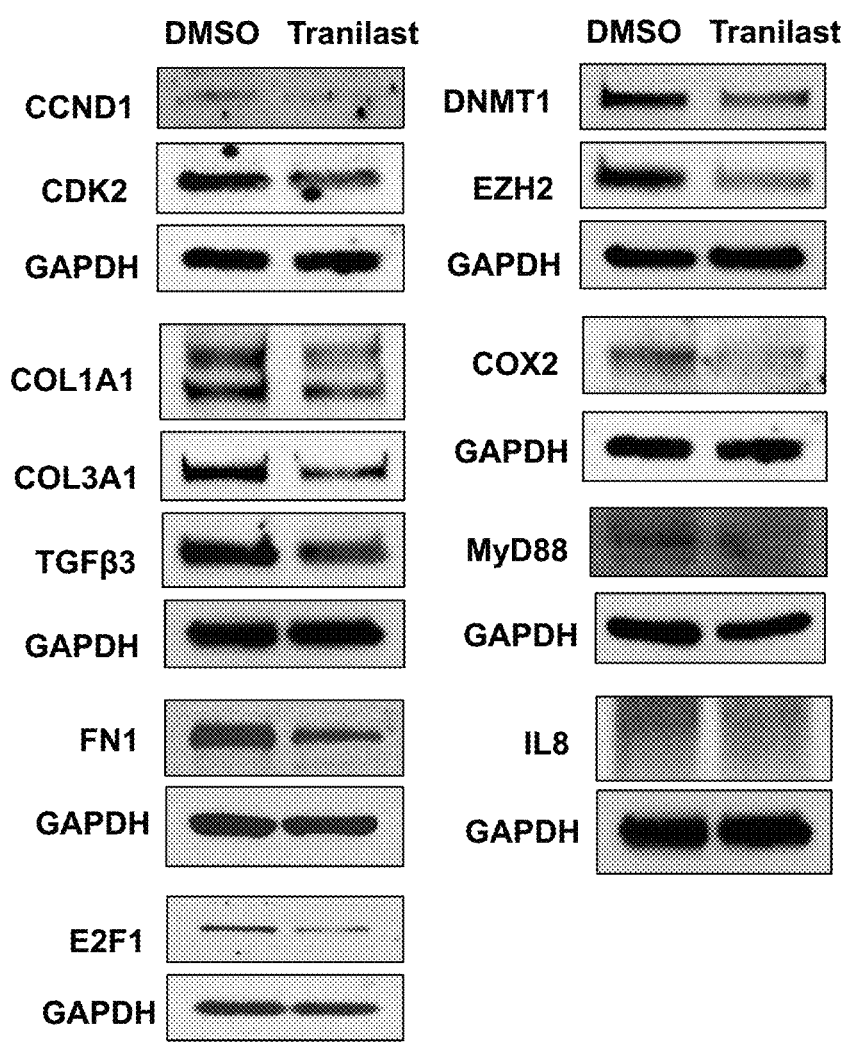
FIG. 4: Representative Western blots for CCND1, CDK2, COL1A1, COL3A1, TGF-β3, FN1, DNMT1, EZH2, COX-2, MyD88, E2F1 and IL8 expression in LSMC treated with Tranilast (200 µM) for 48 h. The results are presented as mean±SEM of at least three independent experiments using LSMC isolated from 3 patients.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}O$, $^{14}$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2 d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

Other definitions of terms may appear throughout the specification.

DETAILED DESCRIPTION

Methods of modulating a miRNA level, such as a miR-29c and/or miR-200c level, in a cell are provided. Aspects of the methods include contacting the cell with an anti-fibrotic miRNA modulating active agent, such as a tranilast active agent. Also provided are compositions for use in practicing the methods. The methods and compositions find use in a variety of applications, including the treatment of fibrotic disorders, such as a uterine leiomyoma.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, methods of modulating a miRNA level in a cell are provided. A miRNA level in a cell is the amount of a given miRNA in cell, e.g., the copy number of a miRNA in a cell. By "modulate" is meant change or alter the level of a miRNA in a cell, e.g., upregulate/increase or downregulate/decrease the level (amount) of a miRNA in a cell. The magnitude of any change may vary, and in some instances is 2 fold or more, such as 10 fold or more, including 25 fold or more, as compared to a suitable control, e.g., as described in the Experimental Section, below. In some instances, the modulation is an increase in the level of one or more miRNAs in a cell. While the magnitude of increase may vary, in some instances the increase, e.g., in copy number, is 25% or more, such as 50% or more, including 75% or more, e.g., 100% or more, as compared to a suitable control, e.g., as described in the Experimental Section, below.

The methods may modulate one or more miRNA levels in a cell. As such, the methods may modulate a single miRNA or two or more distinct miRNAs. Any two miRNAs are distinct if there nucleotide sequences differ by at least one nucleotide residue. In some instances the methods modulate 1 to 5 miRNAs, such as 2 to 4 miRNAs. While the miRNAs that are modulated may vary, miRNAs whose levels may be modulated by methods of the invention include miR-29c (*Homo sapiens* miR-29c Accession No. NR_029832), miR-200c (*Homo sapiens* miR-200c Accession No. NR_029779), etc. In some instances, the methods increase the levels of miR-29c and miR-200c in a cell.

In some instances, the methods include reducing the expression of one or more genes, e.g., genes that regulate cell cycle progression, tissue fibrosis and/or DNA epigenetic methylation, where such genes may include CCND1, CDK2, COL1A1, COL3A1, TGF-β3, DNMT1, EZH2, E2F1, and the like. The magnitude of any change may vary, and in some instances is 2 fold or more, such as 10 fold or more, including 25 fold or more, as compared to a suitable control, e.g., as described in the Experimental Section, below.

Aspects of the methods include contacting the cell in which the miRNA level is to be modulated with an amount of an anti-fibrotic miRNA modulating active agent effective to modulate a miRNA level in the cell. By anti-fibrotic miRNA modulating active agent is meant an agent that has anti-fibrotic activity and modulates a miRNA level, as described above. Examples of anti-fibrotic miRNA modulating active agents include, but are not limited to: tranilast active agents (e.g., tranilast free base or a salt thereof), halofunginone active agents (e.g., halofunginone free base or a salt thereof), perfenidone active agents (e.g., perfenidone free base or a salt thereof), and the like. In some instances, the active agent is not aspirin, bleomycin, amiodarone or BIBF1120.

In some instances, the active agent is a tranilast active agent. Tranilast, (2-[[3-(3,4-dimethoxyphenyl)-1-oxo-2-propenyl]amino]benzoic acid), has the structure shown below:

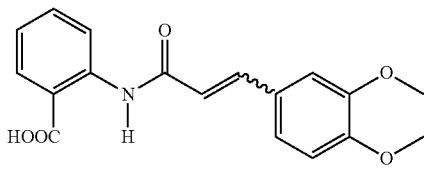 [SMILES: COc1ccc(C=CC(=O)Nc2ccccc2C(=O)O)cc1OC]

A tranilast active agent may be tranilast free base, a salt thereof, or a co-crystal thereof, e.g., as described in published United States patent application publication no. 20170158618 the disclosure of which is herein incorporated by reference.

In practicing methods according to certain embodiments, an effective amount the active agent, e.g., tranilast active agent, such as tranilast free base or salt thereof, is provided in the target cell or cells. In some instances, the effective amount of the active agent is provided in the cell by contacting the cell with the compound. Contact of the cell with the active agent may occur using any convenient protocol. The protocol may provide for in vitro or in vivo contact of the modulatory agent with the target cell, depending on the location of the target cell. In some instances, the cell is in vitro. In certain instances, the cell is in vivo. Contact may or may not include entry of the compound into the cell. For example, where the target cell is an isolated cell, the modulatory agent may be introduced directly into the cell under cell culture conditions permissive of viability of the target cell. The choice of method is generally dependent on the type of cell being contacted and the nature of the compound, and the circumstances under which the transformation is taking place (e.g., in vitro, ex vivo, or in vivo).

Alternatively, where the target cell or cells are part of a multicellular organism, the modulatory agent may be administered to the organism or subject in a manner such that the compound is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are in some cases returned to a living body.

In certain embodiments, the method is an in vivo method that includes administering to a subject in need thereof an effective amount of the active agent. Administration of the subject compounds may be systemic or local. Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal, rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The amount of compound administered can be determined using any convenient method to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of a subject compound is an amount that ranges from about 10 pg to about 500 mg, such as 1 mg to 250 mg, including 5 mg to 150 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 pg, from about 1 pg to about 10 pg, from about 10 pg to about 50 pg, from about 50 pg to about 150 pg, from about 150 pg to about 250 pg, from about 250 pg to about 500 pg, from about 500 pg to about 750 pg, from about 750 pg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, a single dose of the subject compound is administered. In other embodiments, multiple doses of the subject compound are administered. Where multiple doses are administered over a period of time, the active agent may be administered twice daily (qid), daily (qd), every other day (qod), every third day, three times per week (tiw), or twice per week (biw) over a period of time. For example, an active may be administered qid, qd, qod, tiw, or biw over a period of from one day to about 2 years or more. For example, an active agent may be administered at any of the aforementioned frequencies for one week, two weeks, one month, two months, six months, one year, or two years, or more, depending on various factors.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). In some instances, the subject is one that has been diagnosed as having a down regulated miRNA, such as miR-29c, miR-200c, etc.

In some instances, the methods are methods of treating a subject for a condition. The term "treating" or "treatment" as used herein means the treating or treatment of a disease or medical condition in a patient, such as a mammal (such as a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Any of a variety of methods can be used to determine whether a treatment method is effective. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of a target gene or gene product or for the presence of cells that are associated with the disease or condition of interest (e.g., as described herein). The sample can be a cellular sample. In some cases, the sample is a biopsy. The assessment step(s) of the subject method can be performed at one or more times before, during and/or after administration of the subject compounds, using any convenient methods. In certain instances, assessing the subject includes diagnosing whether the subject has a disease or condition of interest. For example, embodiments of the invention may include assessing whether a sample from a subject has one or more down regulated miRNAs, such as miR-29c, miR-200c, etc. Any convenient protocol may be employed for making such an assessment, including the protocols described in the experimental section below. Following such an assessment, the methods may include diagnosing a subject as having a down regulated miRNA, such as miR-29c, miR-200c, etc.

In some instances, the method delays occurrence of a symptom associated with the disease. In certain instances, the method reduces the magnitude of a symptom associated with the disease. The term "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition).

The term "surrogate marker" is employed in its conventional sense to refer to a measure of the effects of specific disease treatment or predict outcomes in a clinical trial. Surrogate markers can be defined as a laboratory measurement or a physical sign that is used in therapeutic trials as a substitute for a clinically meaningful endpoint. Reliable surrogates, rigorously validated in phase III clinical trials, can forecast the long term effect of the therapy based on how the patient feels, functions, or survives (Katz, "Biomarkers and Surrogate Markers: an FDA Perspective," NeuroRx (2004) 1: 189-95). These markers may also be used to compare drug efficacy between trials and may even become the basis for which new drugs gain regulatory approval for marketing (Twaddell, "Surrogate outcome markers in research and clinical practice," Australian Prescriber (2009) 32: 47-50). Because their use can reduce the size, duration, and cost of large studies or clinical trials, these markers are especially valuable if the predicted drug effect prevents death or promotes other critically important outcomes. For some progressive diseases, surrogate markers may be able to determine the disease stage (Weston, "The use of surrogate end points in cardiovascular disease and diabetes," The British Journal of Cardiology (2008) 15: S6-S7). Depending on the specific disease condition, surrogate markers may vary widely. Embodiments of the present disclosure therefore include administering a compound, e.g., as described herein, to modulate, e.g., improve, one or more surrogate markers of the disease condition.

In the subject methods, the active agent may be administered to the targeted cells using any convenient administration protocol capable of resulting in the desired activity, e.g., as described above. Thus, the subject compounds can be incorporated into a variety of formulations, e.g., pharmaceutically acceptable vehicles, for therapeutic administration. As reviewed above, the subject methods result in modulation of miRNA levels, e.g., increase or reduction, in target cell or cells, where the target cell(s) may be in vitro or in vivo.

The above methods find use in a variety of different applications. Certain applications are now reviewed in the following Utility section.

Utility

The subject methods and compound compositions find use in a variety of applications. As such, aspects of the invention include modulating one or more miRNA levels, as described herein, in a subject in need thereof, e.g., a subject that has been diagnosed with a condition that can be treated by effecting one or more of the above outcomes in the subject. Of interest is use of the subject methods and compositions to modify the progression of disease conditions. The phrase "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition).

In some instances, practice of subject methods results in treatment of a subject for a disease condition. By treatment is meant at least an amelioration of one or more symptoms associated with the disease condition afflicting the subject, where amelioration is used in a broad sense to refer to at least a reduction in the magnitude of a parameter, e.g., symptom, associated with the pathological condition being treated, such as loss of cognitive function, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition. Treatment may also manifest in the form of a modulation of a surrogate marker of the disease condition, e.g., as described above.

As indicated above, methods of the invention may be used for the treatment of a variety of different disease condition. In some instances, the disease condition is a fibrotic disorder. Fibrotic disorders are disease conditions characterized by the formation of an abnormal amount of fibrous tissue in an organ or part as the result of inflammation, irritation, or healing. In some instances, the fibrotic disorder is characterized by the presence of a leiomyoma. A leiomyoma, also known as fibroids, is a benign smooth muscle tumor that very rarely becomes cancer (0.1%). They can occur in any organ, but the most common forms occur in the uterus, small bowel, and the esophagus. In some embodiments, the leiomyoma comprises a uterine leiomyoma. As such, embodiments of the methods are methods of treating a subject for a uterine leiomyoma.

Other disease conditions that may be treated by methods of the invention include, but are not limited to: cellular proliferative disease conditions, e.g., cancers and related conditions characterized by abnormal cellular proliferation, e.g., neoplastic diseases and other diseases characterized by the presence of unwanted cellular proliferation, e.g., hyperplasias, and the like; etc.

As reviewed above, a variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs and rats), and primates (e.g., humans, chimpanzees and monkeys). In some embodiments, the host is human.

Pharmaceutical Compositions

Also provided are pharmaceutical preparations of an anti-fibrotic miRNA modulating active agent as described above, such as a tranilast active agent, e.g., for use in methods of the invention. Pharmaceutical preparations are compositions that include an active agent either alone or in the presence of one or more additional active agents present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference.

The choice of excipient will be determined in part by the particular compound, as well as by the particular method used to administer the composition. Accordingly, there is a wide variety of suitable formulations of the subject pharmaceutical compositions.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions.

Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like.

Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

As indicated above, the anti-fibrotic miRNA modulating active agents can be administered to a subject alone or in combination with an additional, i.e., second, active agent, e.g., halofuginone, green tea extracts, and vitamin D. As such, in some cases, the subject method further comprises administering to the subject at least one additional compound. Any convenient agents may be utilized, including compounds useful for treating viral infections. The terms "agent," "compound," and "drug" are used interchangeably herein.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and compounds of the present disclosure.

In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compounds and the second active agent. In pharmaceutical dosage forms, the compounds may be administered in the form of their pharmaceutically acceptable salts, or they may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific compound, the nature of the delivery vehicle, and the like. Preferred dosages for a given compound or agent are readily determinable by those of skill in the art by a variety of means.

Kits & Systems

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. In some embodiments, the subject system or kit includes a dose of a subject compound (e.g., as described herein) and a dose of a second active agent (e.g., as described herein). The various kit components may be present in the containers, e.g., sterile containers, where the components may be present in the same or different containers.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

I. Tranilast Epigenetically Alters the Expression of miR-29c and miR-200c and Inhibits Specific Genes Functionally Involved in Cell Cycle Progression, Tissue Fibrosis and Epigenetic Regulation in Leiomyoma Cells A. Introduction Uterine leiomyomas are the most common pelvic tumors affecting 40-70% of women during their reproductive years. Although their etiology is unknown, leiomyomas are dependent on ovarian steroids for their growth, with symptomatic tumors causing chronic pelvic pain, abnormal uterine bleeding, pelvic pressure, as well as infertility and pregnancy complications. In addition to surgical intervention which accounts for more than 30% (200,000) of all hysterectomies performed in the United States annually, several hormonal therapies have been used as alternative interventions for management of their growth and associated symptoms.

The objective of the present study was to investigate the effect of Tranilast and the molecular mechanism of its action in leiomyoma smooth muscle cells (LSMC). To accomplish this objective the expression of miR-29c and miR-200c, and genes including CCND1, CDK2, COL1A1, COL3A1, TGF-β3, DNMT1 and EZH2, which regulate cell cycle progression, tissue fibrosis and DNA epigenetic methylation were measured. Since DNA hypermethylation is frequently associated with tissue fibrosis and tumorigenesis, we further assessed the effect of Tranilast on the methylation status of miR-29c and miR-200c promoters.

B. Materials and Methods

1. Tissue Collection and Leiomyoma Smooth Muscle Cell Isolation

Leiomyomas and matched myometrium (N=12) were collected from patients scheduled to undergo hysterectomy at Harbor-UCLA Medical Center with prior approval from Institutional Review Board (#036247). The tissues were either snap frozen and stored in liquid nitrogen for further analysis, or used for isolation of LSMC as previously described (Chuang et al., "miR-200c is aberrantly expressed in leiomyomas in an ethnic-dependent manner and targets ZEBs, VEGFA, TIMP2, and FBLN5," Endocrine-related cancer (2012)19:541-56; Chuang et al., "miR-93/106b and their host gene, MCM7, are differentially expressed in leiomyomas and functionally target F3 and IL-8. Molecular endocrinology," (2012) 26:1028-42). Briefly, LSMC were cultured in DMEM supplemented with 10% fetal bovine serum until reaching confluence with a change of media every 2-3 days. Cells at passages p1 to p3 were used for all experiments. Cell culture experiments were performed at least three times using LSMC obtained from different patients. All supplies for isolation and cell culture were purchased from Sigma-Aldrich (St. Louis, Mo.), Invitrogen (Carlsbad, Calif.) and Fisher Scientific (Atlanta, Ga.).

2. Cell Proliferation Assay

LSMC were seeded at 1000 cells/well in 96-well plates and cultured for 48 hrs. The cells were then treated with 100 to 400 μM Tranilast at sub-confluence for 48 hrs. The rate of cell proliferation was determined using the MTT assay and cells were photographed as previously described (Chuang & Khorram, "Mechanisms underlying aberrant expression of miR-29c in uterine leiomyoma," Fertility and sterility (2016)105:236-45.e1; Chuang et al., "The Regulatory Function of miR-200c on Inflammatory and Cell-Cycle Associated Genes in SK-LMS-1, A Leiomyosarcoma Cell Line," Reproductive sciences (2015) 22:563-71). Briefly, MTT (Sigma-Aldrich) was added to the culture medium at a final concentration of 1 mg/ml and incubated for 2 hrs at 37° C. The medium was aspirated, and the formazan product was solubilized with dimethyl sulfoxide and the absorbance at 570 nm was determined and subtracted from the absorbance at 630 nm (background) for each well. The assay was performed in six replicates per condition and repeated three times.

3. Caspase-3/7 Activity Assay

LSMC were cultured in 96-well plates as mentioned above and at sub-confluence were treated with 200 μM Tranilast for 48 hrs. The caspase 3/7 activity was determined using the Apo-One homogeneous caspase-3/7 assay (Promega, Madison, Wis.) after the indicated time periods according to the manufacturer's protocol. The Apo-One caspase-3/7 reagent was added in a 1:1 ratio with the medium, and the rate of caspase-3/7 activity was determined by measuring the fluorescence using a multi-plate reader (Molecular Devices, Inc., Sunnyvale, Calif.) at an excitation of 485 nm and an emission of 527 nm.

4. RNA Isolation and Quantitative RT-PCR Analysis

Total RNA was extracted from LSMC using RNAzol (GeneCopoeia, Rockville, Md.) and their quantity and quality was determined (ND-1000 Spectrophotometer, Nano-Drop Technologies, Wilmington, Del.) as previously described (Chuang & Khorram, "miR-200c Regulates IL8 Expression by Targeting IKBKB: A Potential Mediator of Inflammation in Leiomyoma Pathogenesis," PloS one (2014) 9:e95370). For medium miRNA extraction, 5 pg of synthetic miR-1 from *Caenorhabditis elegans* (cel-miR-1) was added as a spike-in control for purification efficiency. Subsequently, 2 μg or 10 ng (for miRNA) was reverse transcribed using random primers for CCND1, CDK2, COL1A1, COL3A1, TGF-β3, DNMT1 and EZH2 or specific primers for miR-29c and miR-200c according to the manufacturer's guidelines (Applied Biosystems, Carlsbad, Calif.). Quantitative RT-PCR was carried out using SYBR gene expression master mix or TaqMan miRNA expression assays (Applied Biosystems). Reactions were incubated for 10 min at 95° C. followed by 40 cycles for 15 seconds at 95° C. and 1 min at 60° C. The level of mRNAs and expression of cellular and secreted miRNA was determined using the Invitrogen StepOne System with 18S, RNU6B and cel-miR-1 used for normalization respectively. All reactions were run in triplicate and relative expression was analyzed with the comparative cycle threshold method ($2^{-\Delta\Delta CT}$) according to the manufacturer (Applied Biosystems). Values were expressed as fold change compared to the control group. The primer sequences used were as follows:

```
CCND1
(sense, 5'-GCCCTCTGTGCCACAGATGT-3'
(SEQ ID NO: 01);

antisense, 5'-CCCCGCTGCCACCAT-3'
(SEQ ID NO: 02));

CDK2
(sense, 5'-TTCCCCTCATCAAGAGCTATCTGT-3'
(SEQ ID NO: 03);

antisense, 5'-ACCCGATGAGAATGGCAGAA-3'
(SEQ ID NO: 04));

COL1A1
(sense, 5'-CCAATGGTGCTCCTGGTATT-3'
(SEQ ID NO: 05;

antisense, 5'-GTTCACCGCTGTTACCCTT-3'
(SEQ ID NO: 06));

COL3A1
(sense, 5'-ATTATTTTGGCACAACAGGAAGCT-3'
(SEQ ID NO: 07);

antisense, 5'-TCCGCATAGGACTGACCAAGAT-3'
(SEQ ID NO: 08));

TGF-β3
(sense, 5'-CGGGCTTTGGACACCAATTA-3'
(SEQ ID NO: 09);

antisense, 5'-GGGCGCACACAGCAGTTC-3'
(SEQ ID NO: 10));

DNMT1
(sense, 5'-GAACCAACGGAGAAAAAATGG-3'
(SEQ ID NO: 11);

antisense, 5'-GGGAGGGTGGGTCTTGGA-3'
(SEQ ID NO: 12)),

EZH2
(sense, 5'-GGAGGATCACCGAGATGATAAAG-3'
(SEQ ID NO: 13);

antisense, 5'-TTCTGCTGTGCCCTTATCTG-3'
(SEQ ID NO: 14))
and 18S
(sense, 5'-CGAGCCGCCTGGATACC-3'
(SEQ ID NO: 15);

antisense, 5'-CAGTTCCGAAAACCAACAAAATAGA-3'
(SEQ ID NO: 16)).
```

4. Immunoblotting

Total protein isolated from LSMC treated with Tranilast (200 μM) at sub-confluence for 48 hrs and from tissues was subjected to immunoblotting as previously described (Chuang et al., "miR-29c induction contributes to downregulation of vascular extracellular matrix proteins by glucocorticoids," American journal of physiology Cell physiology (2015) 309:C117-25). Specific antibodies generated against CCND1, COL3A1, TGF-β3 (Proteintech Group, Inc., Chicago, Ill.), CDK2, DNMT1 (Santa Cruz Biotechnology, Dallas, Tex.), COL1 (Fitzgerald Industries Intl., Acton, Mass.) and EZH2 (Cell Signaling Technology, Danvers, Mass.) were used to detect specific protein expression. The membranes were also stripped and probed with GAPDH antibody (Proteintech Group, Inc.) serving as loading control.

5. Methylation-specific PCR

LSMC at sub-confluence were treated with Tranilast (200 μM) for 24 hrs and genomic DNA was extracted and treated with bisulfite (EZ DNA Methylation Kit, Zymo Research Corporation, Irvine, Calif.). Since methylated cytosine residues remained unchanged after bisulfite conversion, this approach allows distinguishing DNA sequences which are methylated or unmethylated in specific genomic regions using sequence-specific PCR primers (Li & Dahiya, "MethPrimer: designing primers for methylation PCRs," Bioinformatics (2002)18:1427-31). The pair of primers used to detect the methylated (Me) sequence of miR-29c promoter were 5'-GATGGGATTAAATTTTGGAATATTC-3' (SEQ ID NO:17) and 5'-AAATCCTAAAACCCGTCGAA-3' (SEQ ID NO:18) and for the unmethylated (Un) sequence of miR-29c promoter were 5'-GGGATTAAATTTTGGAAT-ATTTGG-3' (SEQ ID NO:19) and 5'-ATCAAATC-CTAAAACCCATCAAA-3' (SEQ ID NO:20). The pair of primers used to detect the methylated (Me) sequence of miR-200c promoter were 5'-GAATTTGGGGTTT-TAAAGTTTTTTC-3' (SEQ ID NO:21) and 5'-CAC-CCTAAATCGCTAATCACG-3' (SEQ ID NO:22), and for the unmethylated (Un) sequence of miR-200c promoter were 5'-GAATTTGGGGTTTTAAAGTTTTTTT-3' (SEQ ID NO:23) and 5'-CACACCCTAAATCACTAATCA-CAAA-3' (SEQ ID NO:24). DNA amplification was carried out following manufacturer's protocol (HotStarTaq Plus PCR reagent, Qiagen, Valencia, Calif.). The PCR condition was 5 min at 95° C., followed by 40 cycles of amplification at 94° C. for 30 seconds, 30 seconds at 55° C., and 1 min at 72° C. PCR amplified products were electrophoresed on 2% agarose gel and visualized under ultraviolet illumination.

6. Luciferase Reporter Assays

LSMC were seeded at $3.5 \times 10^4$ cells/well in 6-well plates and at sub-confluence were treated with Tranilast (200 μM) or DMSO as control for 48 hrs. Tranilast and DMSO-treated cells were then transfected with luciferase reporter plasmids (1 μg/well) containing 3' UTR sequences for COL3A1 or CDK2 (GeneCopoeia, Inc., Rockville, Md.) using PureFection transfection reagent (System Biosciences, Inc., Palo Alto, Calif.). After 48 hrs of transfection Firefly and *Renilla* luciferase activities were measured using the Dual-Luciferase Reporter Assay System (Promega). Firefly luciferase activity was normalized to *Renilla* luciferase activity. The level of induction was reported as mean±SEM of three experiments and compared with a ratio in cells treated with DMSO independently set as 1.

7. Statistical Analysis

Throughout the text, results are reported as mean±SEM and analyzed by PRISM software (Graph-Pad, San Diego, Calif.). Dataset normality was determined by the Kolmogrove-Smirnoff test. Comparisons involving two groups were analyzed using unpaired Student's t-tests. For comparisons involving multiple groups, one way ANOVA was used with Tukey's HSD for post hoc analysis. Statistical significance was established at $P<0.05$.

C. Results

1. Tranilast Inhibits LSMC Proliferation without Affecting Caspase 3/7 Activity

We first analyzed the influence of Tranilast on the rate of LSMC proliferation. As shown in FIGS. 1A and 1B, Tranilast in a dose-dependent manner significantly inhibited the rate of LSMC cell proliferation (p<0.05), without a significant effect on Caspase 3/7 activity after 48 hrs of treatment (FIG. 1C). The results show that Tranilast suppressed primary leiomyoma smooth muscle cells (LSMC) proliferation, not through induction of apoptosis.

2. Tranilast Inhibits the Expression of CCND1, CDK2, ECM, TGF-β3, DNMT1 and EZH2

Prior to examining the effect of Tranilast on the expression of cell cycle-related genes, ECM, TGF-β3, DNMT1 and EZH2, in isolated LSMC we assessed their expression in leiomyomas. As shown in FIGS. 2A and 2B, leiomyomas expressed elevated levels of CCND1, CDK2, COL1, COL3, TGF-β3, DNMT1 and EZH2 as compared to matched myometrium (P<0.05). The results show that Leiomyoma express elevated levels of CCND1, CDK2, COL1A1, COL3A1, TGF-β3, DNMT1, EZH2, MyD88, FN1 and E2F1 as compared to matched myometrium.

Since Tranilast inhibited LSMC proliferation and progression into cell-cycle is regulated through the expression of various genes, including CCND1 and CDK2, we examined and found that Tranilast significantly inhibited the expression of CCND1 and CDK2 in LSMC at both mRNA and protein levels (P<0.05; FIGS. 3A and 3B and 4). Additionally, overexpression of extracellular matrix, including collagens and pro-fibrotic cytokines, TGF-β3, play a central role in pathogenesis of leiomyomas and DNMTs and EZH2 are key elements in epigenetic regulation of protein-coding genes and miRNAs expression. As shown in FIG. 3A, treatment of LSMC with Tranilast significantly inhibited the expression of COL1, COL3A1 and TGF-β3 as well as DNMT1 and EZH2 expression at mRNA and protein levels (P<0.05; FIGS. 3A and 3B).

3. Tranilast Altered the Expression of Cellular and Secreted miR-29c and miR-200c and Methylation Status of their Promoters We have previously reported that the expression of miR-29c and miR-200c is suppressed in leiomyomas as compared to myometrium (Chuang et al., "miR-200c is aberrantly expressed in leiomyomas in an ethnic-dependent manner and targets ZEBs, VEGFA, TIMP2, and FBLN5," Endocrine-related cancer (2012)19:541-56; Chuang et al., "miR-93/106b and their host gene, MCM7, are differentially expressed in leiomyomas and functionally target F3 and IL-8. Molecular endocrinology," (2012) 26:1028-42). As shown in FIGS. 5A and 5B, Tranilast significantly increased the expression of cellular and secreted miR-29c and miR-200c in LSMC (P<0.05). However, as shown in FIG. 5C, miR-29c level was not affected after treatment with other anti-inflammatory agents (Aspirin), anti-fibrotic agent (BIBF 1120) and agents inducing fibrosis (bleomycin and amiodarone) indicating the specificity of Tranilast.

Figure 6:
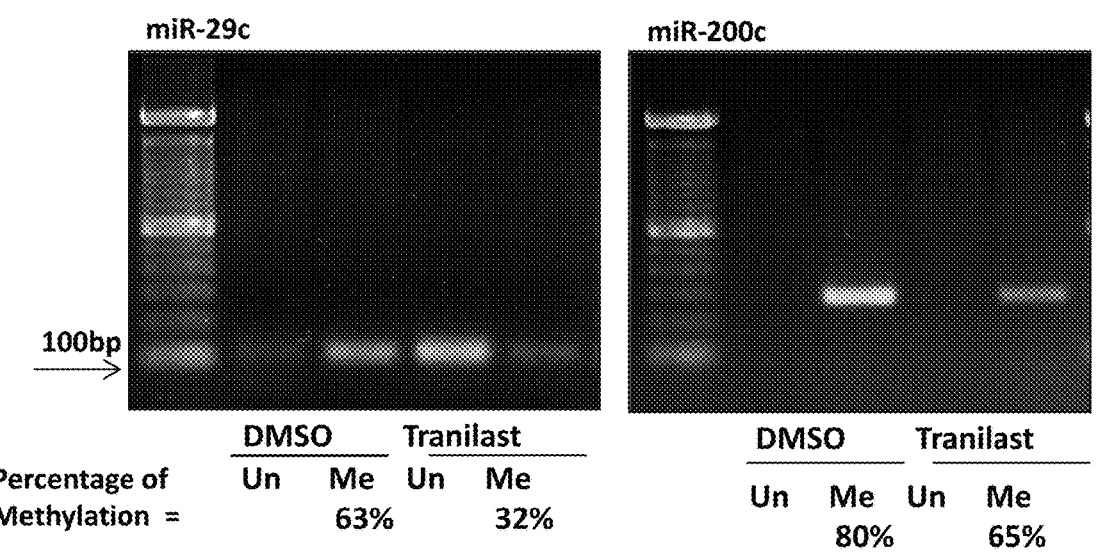
FIG. 6: Methylation-specific-PCR shows Tranilast (200 µM) mediated decrease miR-29c and miR-200c promoter methylation after 24 hrs of incubation. The bands were quantified with NIH Image J software and the percentage of methylation was calculated as: Methylation/Methylation+ Unmethylation (Me/Me+Un).

Since the expression of miR-29c and miR-200c expression are epigenetically regulated, we further examined whether induction of miR-29c and miR-200c by Tranilast in LSMC is mediated by epigenetic modification. As shown in FIG. 6, Tranilast significantly suppressed the methylation status in miR-29c and miR-200c promoters in LSMC after 24 hrs of treatment (P<0.05).

4. Among the Genes Up-regulated in Leiomyoma COL3A1, COL1A1, CDK2 and TGFβ3 are Targets of miR-29c; and CDK2, IL8, MyD88 and FN1 are Targets of miR-200c FIG. 7A: Complementary sequences between miR-29c and 3'UTR of COL3A1, COL1A1, CDK2 and TGFβ3. FIG. 7(B): The relative luciferase activity in isolated leiomyoma smooth muscle cells (LSMC) co-transfected with Renilla and firefly luciferase reporter carrying a 3'UTR fragment of COL3A1, COL1A1, CDK2 and TGFβ3, pre-miR-29c or control oligonucleotides (NC) for 48 hrs. The relative luciferase activity is presented as the ratio of Firefly:Renilla as compared to NC which was independently set as 1. The results are presented as mean±SEM of at least three independent experiments with p values (*P<0.05) indicated by corresponding lines.

FIG. 8A: Complementary sequences between miR-200c and 3'UTR of CDK2, IL8, MyD88 and FN1. FIG. 8B: The relative luciferase activity in LSMC (for CDK2) and SK-LMS-1 (for IL8) co-transfected with Renilla and firefly luciferase reporter carrying a 3'UTR fragment of CDK2, IL8, pre-miR-200c or control oligonucleotides (NC) for 48 hrs. The relative luciferase activity is presented as the ratio of Firefly:Renilla as compared to NC which was independently set as 1. The results are presented as mean±SEM of at least three independent experiments with p values (*P<0.05) indicated by corresponding lines.

Figure 9:
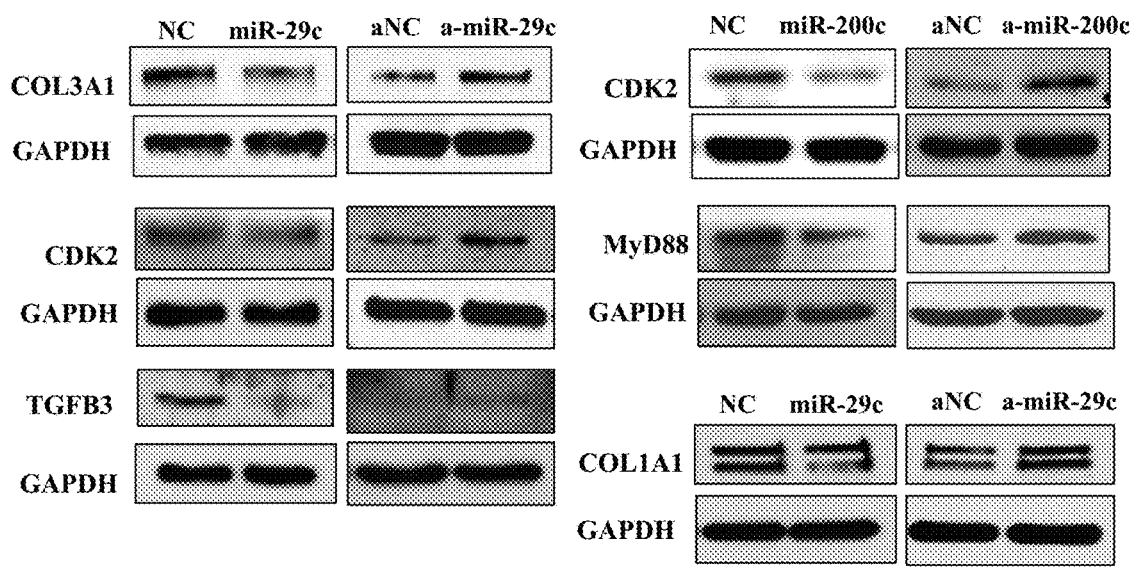
FIG. 9: Western blot analysis of COL3A1, CDK2, TGFβ3, COL1A1 and MyD88 following transfection of LSMC with pre-miR-29c, pre-miR-200c, anti-miR-29c (a-miR-29c) or anti-miR-200c (a-miR-200c) oligonucleotides for 96 hours. The results are presented as a representative of at least three independent experiments using LSMC isolated from 3 patients.

FIG. 9: Western blot analysis of COL3A1, CDK2, TGFβ3, COL1A1 and MyD88 following transfection of LSMC with pre-miR-29c, pre-miR-200c, anti-miR-29c (a-miR-29c) or anti-miR-200c (a-miR-200c) oligonucleotides for 96 hours. The results are presented as a representative of at least three independent experiments using LSMC isolated from 3 patients.

4. Tranilast Down-regulated Expression of COL3A1, CDK2 or IL8 in Part Through induction of miR-29c and miR-200c.

Figure 10A:
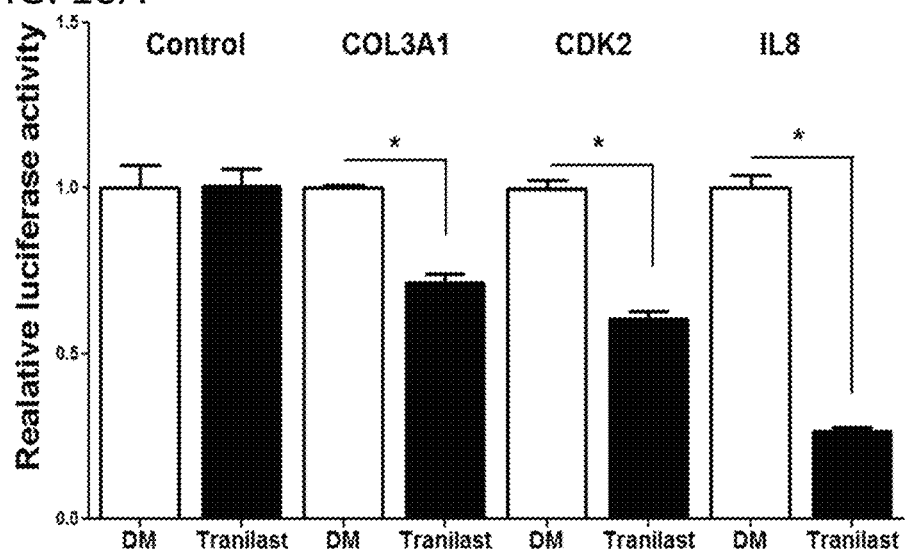
FIG. 10A: The relative luciferase activity in LSMC treated with Tranilast (200 µM) or DMSO as control for 48 hrs prior to transfection with *Renilla* and Firefly luciferase reporter plasmids carrying a 3'UTR fragment of COL3A1, CDK2 or IL8 and incubated with Tranilast (200 µM) or DMSO containing medium after transfection for another 48 hrs. The relative luciferase activity is presented as the ratio of Firefly:*Renilla* as compared to DMSO which was independently set as 1. The results are presented as mean±SEM of at least three sets of independent experiments using LSMC isolated from 3 patients.
Figure 10B:
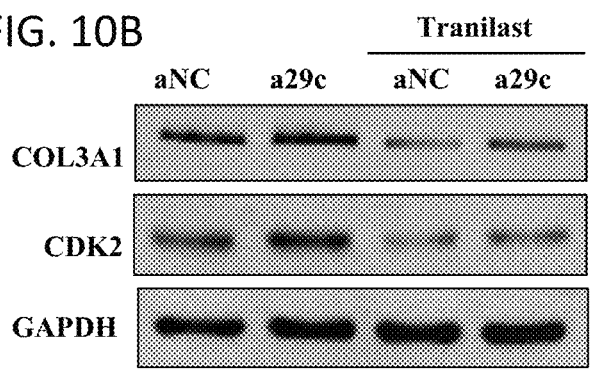
FIG. 10B: Protein expression of COL3A1 and CDK2 was determined after transfection of anti-miR scrambled oligonucleotides (aNC) or anti-miR-29c oligonucleotides (a29c) in LSMC for 72 hrs with DMSO or Tranilast (200 µM) treatment for the last 48 hrs. GAPDH was used as loading control. The result is one representative of at least three sets of independent experiments using LSMC isolated from 3 patients.
Figure 10C:
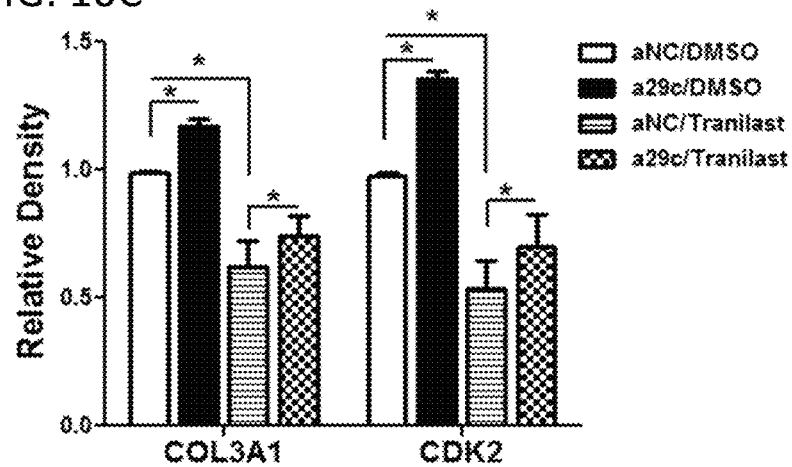
FIG. 10C: The bar graph presented the relative band densities as mean±SEM of at least three independent experiments. Inhibition of protein expression by Tranilast treatment was calculated relative to changes in corresponding DMSO controls in cells transfected with aNC or anti-miR-29c.
Figure 11:
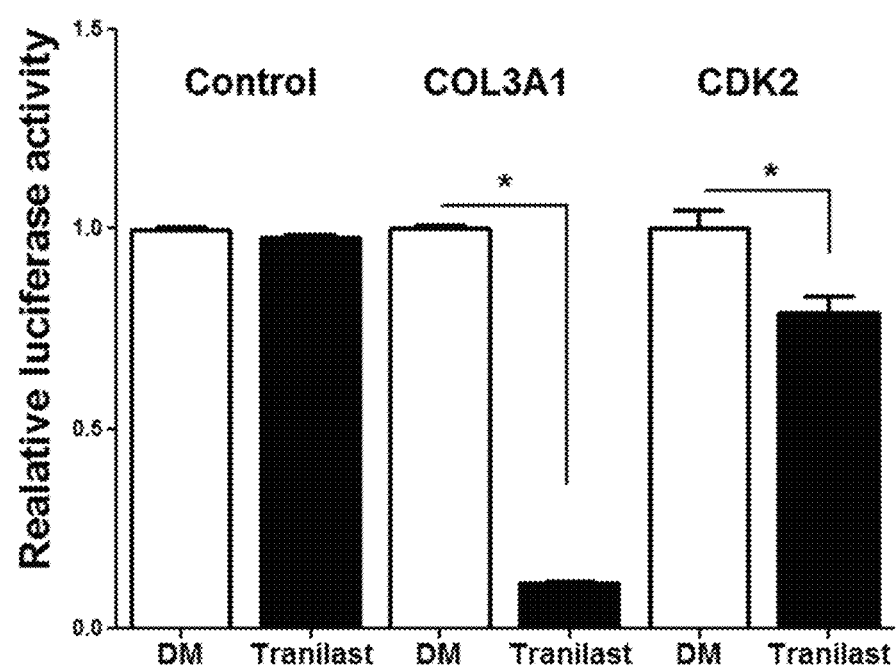
FIG. 11: Tranilast Inhibits the activity of luciferase reporter containing 3'UTR of COL3A1 and CDK2, which are targets of miR-29c and miR-200c, respectively, in lung cancer cell line A549.

FIG. 10A: The relative luciferase activity in LSMC treated with Tranilast (200 μM) or DMSO as control for 48 hrs prior to transfection with Renilla and Firefly luciferase reporter plasmids carrying a 3'UTR fragment of COL3A1, CDK2 or IL8 and incubated with Tranilast (200 μM) or DMSO containing medium after transfection for another 48 hrs. The relative luciferase activity is presented as the ratio of Firefly:Renilla as compared to DMSO which was independently set as 1. The results are presented as mean±SEM of at least three sets of independent experiments using LSMC isolated from 3 patients. FIG. 10B: Protein expression of COL3A1 and CDK2 was determined after transfection of anti-miR scrambled oligonucleotides (aNC) or anti-miR-29c oligonucleotides (a29c) in LSMC for 72 hrs with DMSO or Tranilast (200 μM) treatment for the last 48 hrs. GAPDH was used as loading control. The result is one representative of at least three sets of independent experiments using LSMC isolated from 3 patients. FIG. 10C: The bar graph presented the relative band densities as mean±SEM of at least three independent experiments. Inhibition of protein expression by Tranilast treatment was calculated relative to changes in corresponding DMSO controls in cells transfected with aNC or anti-miR-29c.

5. Inhibitory Effects of Tranilast are not Limited to Leiomyoma Cells

Tranilast Inhibits the activity of luciferase reporter containing 3'UTR of COL3A1 and CDK2, which are targets of miR-29c and miR-200c, respectively, in lung cancer cell line A549, indicating that the inhibitory effects of Tranilast are not limited to leiomyoma cells.

6. Tranilast Induced miR-29c Expression through Epigenetic Mechanism.

Figure 12A:
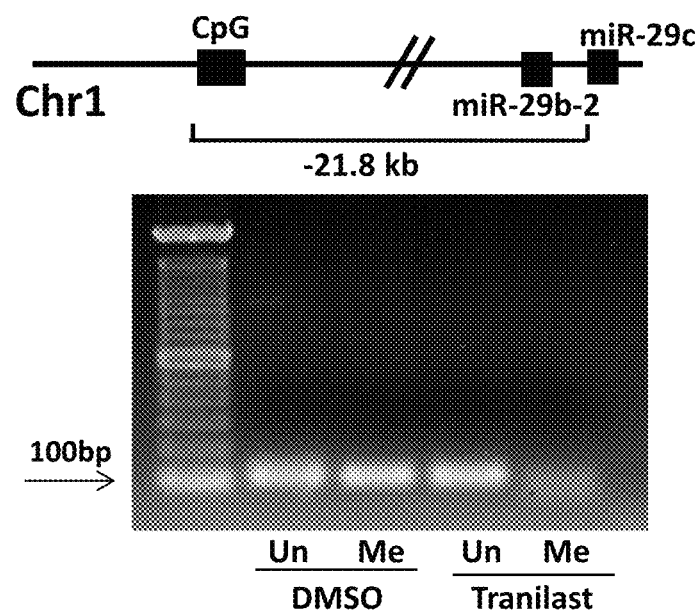
FIG. 12A: Graphical depiction of the miR-29b-2/29c with the location of "CpG" indicated the regions tested for DNA methylation status in miR-29c promoters. One representative of Methylation-specific-PCR result shows Tranilast (200 µM) mediated decrease miR-29c promoter methylation after 24 hrs of incubation.
Figure 12B:
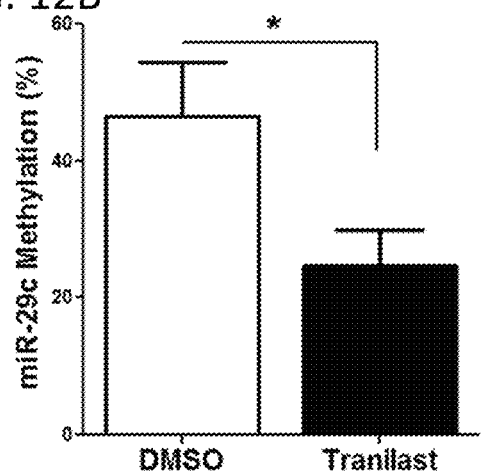
FIG. 12B The bands were quantified with NIH Image J software and the percentage of methylation was calculated as: Methylation/Methylation+Unmethylation (Me/Me+Un). The results are presented as mean±SEM of at least three independent experiments using LSMC isolated from 3 patients.

FIG. 12A: Graphical depiction of the miR-29b-2/29c with the location of "CpG" indicated the regions tested for DNA methylation status in miR-29c promoters. One representative of Methylation-specific-PCR result shows Tranilast (200 μM) mediated decrease miR-29c promoter methylation after 24 hrs of incubation. FIG. 12B The bands were quantified with NIH Image J software and the percentage of methylation was calculated as: Methylation/Methylation+ Unmethylation (Me/Me+Un). The results are presented as mean±SEM of at least three independent experiments using LSMC isolated from 3 patients.

7. Tranilast Induced miR-200c Expression Through Blockade of NF-kB Signaling.

Figure 13A:
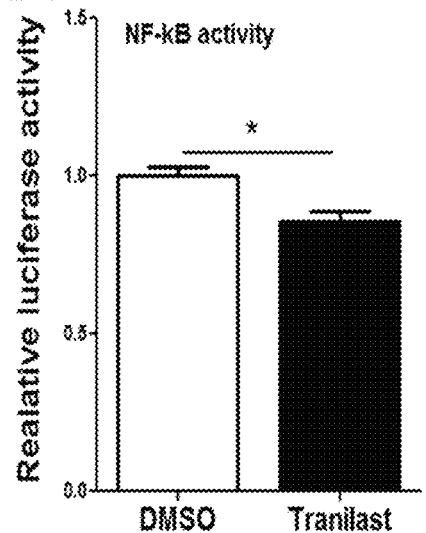
FIG. 13A shows the level of NF-kB activity in LSMC transfected with a luciferase reporter construct containing preserved NF-kB binding sites and pRL-TK as transfection efficiency control. The ratio of Firefly:$Renilla$ was determined after treatment of Tranilast (200 µM) for 48 hrs and reported as relative luciferase activity as compared to DMSO which was independently set as 1.
Figure 13B:
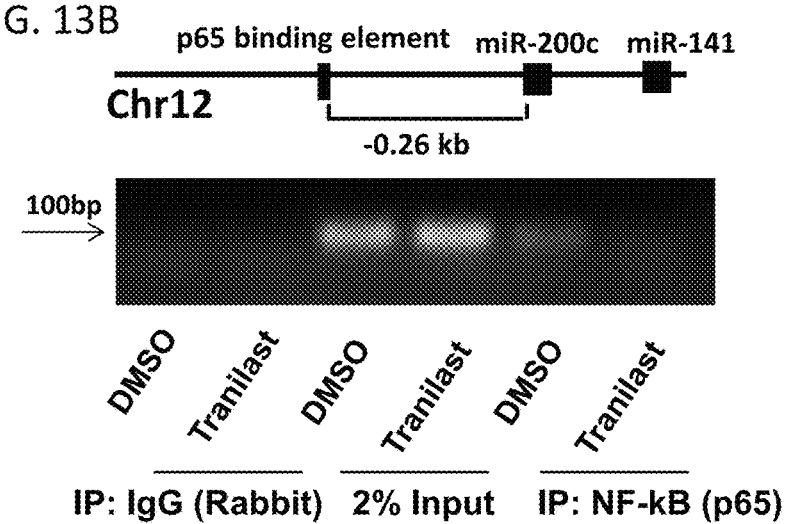
FIG. 13B: Graphical depiction of the NF-Kb (p65) binding elements in the miR-200c promoter. One representative of CHIP assay result shows Tranilast (200 µM) decreased p65 binding ability after 48 hrs of incubation in LSMC and the analysis was presented by percent input method shown in FIG. 13C. The results are presented as mean±SEM of at least three independent experiments using LSMC isolated from 3 patients.
Figure 13C:
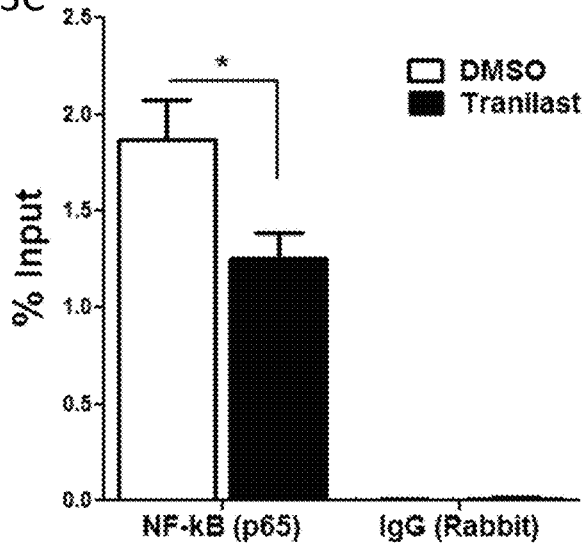

FIG. 13A shows the level of NF-kB activity in LSMC transfected with a luciferase reporter construct containing preserved NF-kB binding sites and pRL-TK as transfection efficiency control. The ratio of Firefly:Renilla was determined after treatment of Tranilast (200 μM) for 48 hrs and reported as relative luciferase activity as compared to DMSO which was independently set as 1. FIG. 13B: Graphical depiction of the NF-Kb (p65) binding elements in the miR-200c promoter. One representative of CHIP assay result shows Tranilast (200 μM) decreased p65 binding ability after 48 hrs of incubation in LSMC and the analysis was presented by percent input method shown in FIG. 13C. The results are presented as mean±SEM of at least three independent experiments using LSMC isolated from 3 patients.

9. Halofuginone and Pirfinidone have Similar Activity to Tranilast

Figure 14:
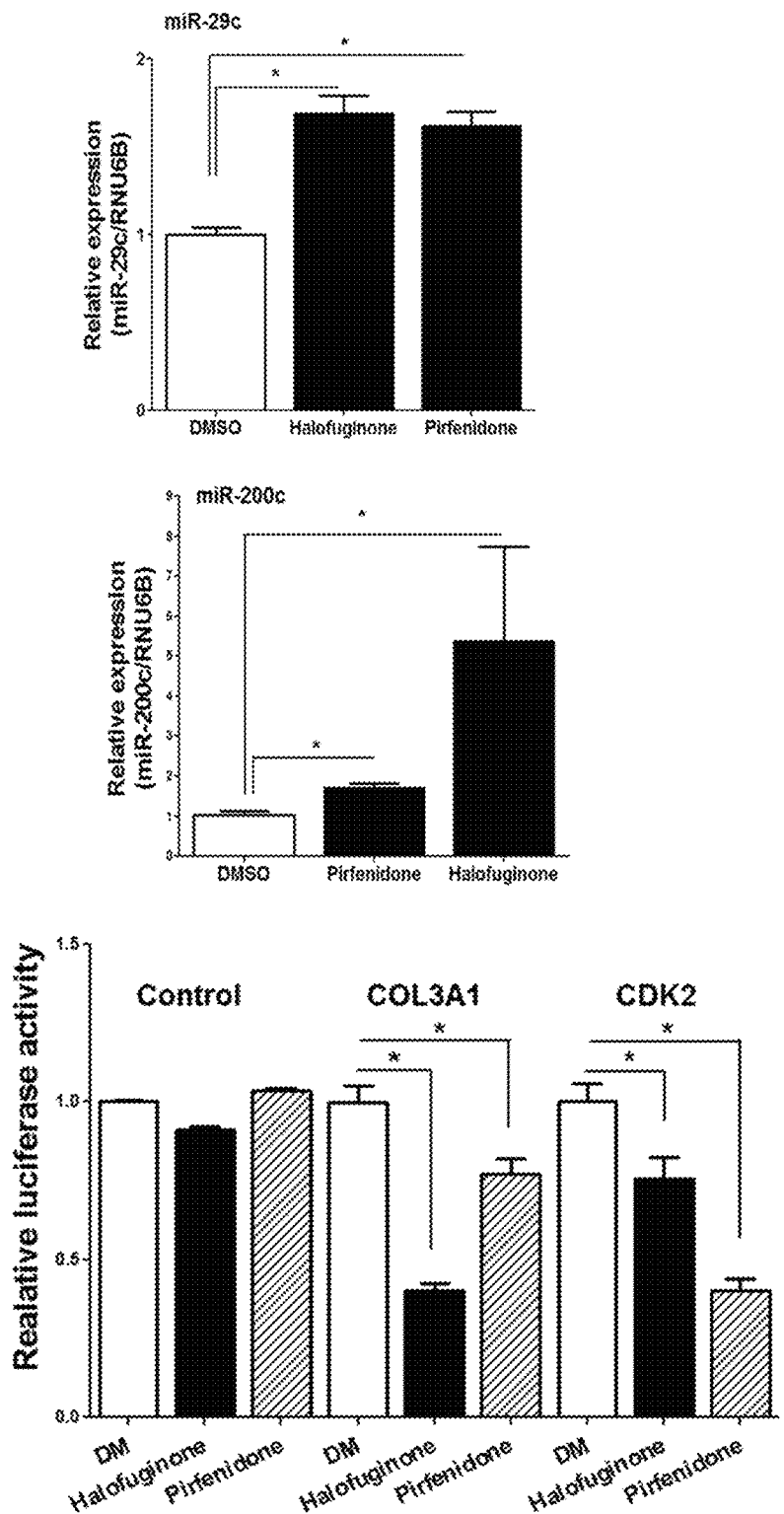
FIG. 14: Halofuginone (200 nM) and Pirfenidone (0.25 mg/ml) induce expression of miR-29c and miR-200c and inhibit the activity of luciferase reporter containing 3'UTR of COL3A1 and CDK2, which are targets of miR-29c and miR-200c, respectively, in primary leiomyoma cells. The results show that two other antifibortic drugs have results are similar to tranilast and indicate a common mechanism by which anti-fibrotic agents work through namely miR29c and 200.

FIG. 14: Halofuginone (200 nM) and Pirfenidone (0.25 mg/ml) induce expression of miR-29c and miR-200c and inhibit the activity of luciferase reporter containing 3'UTR of COL3A1 and CDK2, which are targets of miR-29c and miR-200c, respectively, in primary leiomyoma cells. The results show that two other antifibortic drugs have results are similar to tranilast and indicate a common mechanism by which anti-fibrotic agents work through namely miR29c and 200.

8. Summary

In sum, Tranilast significantly inhibited the rate of LSMC proliferation, which was associated with down-regulation of cell cycle progression genes CCND1 and CDK2 expression at mRNA and protein levels (P<0.05). Tranilast also suppressed the expression of COL1A1, COL3A1, the pro-fibrotic cytokine, TGF-β3, and DNMT1 and EZH2, which regulate epigenetic status of gene promoters (P<0.05). Tranilast significantly induced the expression of cellular and secreted miR-29c and miR-200c through down-regulation of methylation status of their promoters (P<0.05). Tranilast also suppressed the 3'UTR activity of COL3A1 and CDK2, downstream targets of miR-29c and miR-200c respectively (P<0.05).

D. Discussion

In the present study we demonstrated that in isolated LSMC, Tranilast inhibited the rate of cell proliferation and the expression of several genes functionally associated with cell-cycle progression (CCND1 and CDK2), ECM accumulation (COL1A1 and COL3A1), tissue fibrosis associated cytokine (TGF-β3), and enzymes (DNMT1 and EZH2) involved in DNA epigenetic modification. The significance of our findings relates to overall key regulatory function of these gene products in the outcome of tissue fibrosis which is a well-established characteristic of leiomyomas. As such, we provide evidence showing that the expression of CCND1, CDK2, COL1A1, COL3A1, TGF-β3, DNMT1 and EZH2 are elevated in leiomyomas as compared to matched myometrium. In regards to the inhibitory action of Tranilast on LSMC proliferation, our results provide evidence that the inhibitory action of Tranilast in LSMC involves downregulation of CCND1 at both transcriptional and translational levels. Tranilast did not have a significant effect on caspase 3/7 activity in LSMC which shows a lack of effect of Tranilast on apoptosis in LSMC. In addition to cell proliferation, the accumulation of ECM whose expression is regulated by various pro-fibrotic cytokines such as TGF-β family is critical to the outcome of progressive fibrotic disorders, including leiomyomas. Our results provide support for elevated expression of COL1A1, COL3A1 and TGF-β3 in leiomyoma as compared to myometrium and inhibition of their expression by Tranilast at both transcriptional and translational levels in isolated LSMC.

We also demonstrated for the first time that Tranilast significantly induced the expression of miR-29c and miR-200c in LSMC. The significance of these results relates to a well-established regulatory function of miRNAs which through post-transcriptional regulation of protein-coding genes play key roles in many aspects of normal cellular activities. Conversely, altered expression of miRNAs has been associated with a wide range of disorders, including tissue fibrosis and tumorigenesis. Expression profiling has demonstrated altered expression of many miRNAs, including lower expression of miR-29c and miR-200c in leiomyomas compared to myometrium. The significance of Tranilast induction of miR-29c and miR-200c expression relates to regulatory functions of these miRNAs on the expression of many of their target genes, including several ECM-, cell cycle- and apoptosis-related genes, and genes involved in phenotypic cellular transition, including fibroblast to myofibroblast transition, inflammation, and angiogenesis. We have previously reported that low expression of miR-29c and miR-200c in leiomyomas was inversely correlated with the expression of several of their target genes (Chuang et al., "miR-200c is aberrantly expressed in leiomyomas in an ethnic-dependent manner and targets ZEBs, VEGFA, TIMP2, and FBLN5," Endocrine-related cancer (2012)19: 541-56; Chuang et al., "miR-93/106b and their host gene, MCM7, are differentially expressed in leiomyomas and functionally target F3 and IL-8. Molecular endocrinology," (2012) 26:1028-42). Since COL3A1 and CDK2 are known as direct targets of miR-29c and miR-200c, respectively, as a proof of principle we selected these genes and using 3'UTR luciferase reporter assay demonstrated that the inhibition of their expression at least in part occurred through alteration of their 3'UTRs activities in LSMC. The results showed that upregulation of miR-29c and miR-200c by Tranilast can result in downregulation of their known target genes such as COL3A1 and CDK2 and potentially other genes predicted as targets of these miRNAs.

Our results indicate that induction of miR-29c and miR-200c expression in LSMC by Tranilast is mediated at least in part through a mechanism involving de-methylation of their promoters. Both DNA methylation and histone modification through epigenetic mechanism play an important regulatory function in gene and miRNA expression thereby influencing various normal cellular activities and potential pathological outcomes. Previous studies have demonstrated that DNA methylation patterns and DNA methyltransferases (DNMTs) expression are altered in leiomyomas as compared with myometrium. Additionally, histone methyltransferase EZH2, a catalytic subunit of Polycomb Repressor Complex 2 (PRC2), catalyzes methylation of histone H3 at lysine 27 (H3K27me) through cooperation with PRC1, DNMTs and histone deacetylase (HDAC), thus causing gene silencing of target genes via local chromatin reorganization. Here we showed for the first time that Tranilast inhibited the expression of DNMT1 and EZH2 at transcriptional and translational levels. These results further suggest that elevated expression of DNMT1 and EZH2 in leiomyomas could induce hyper-methylation in miR-29c and miR-200c promoters with resultant reduced expression of these miRNAs.

Figure 15:
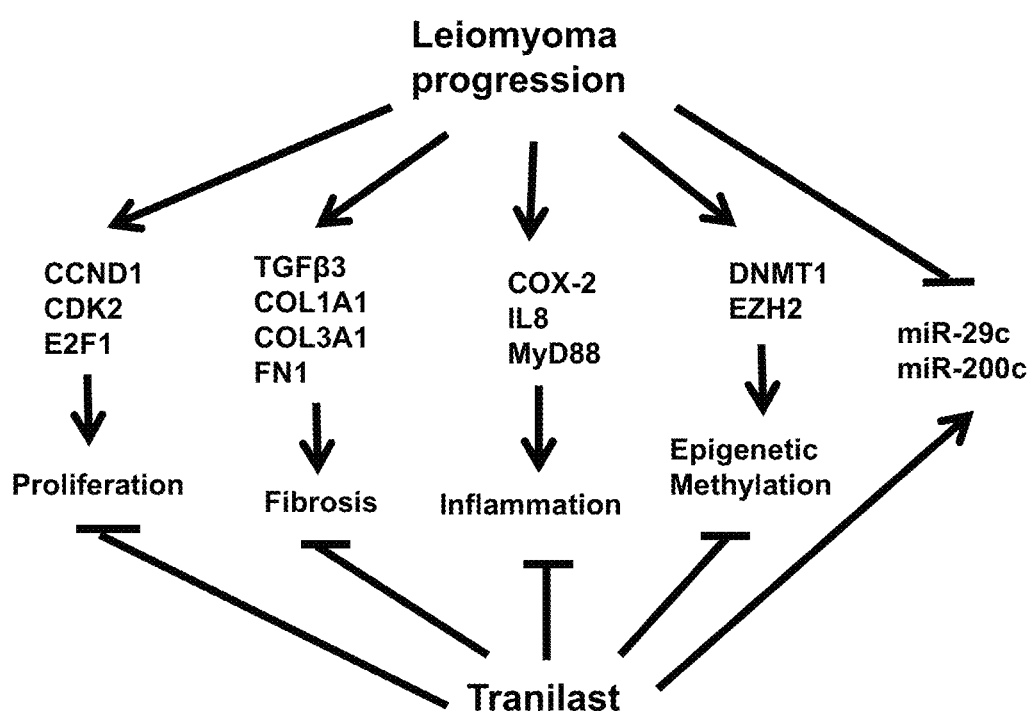
FIG. 15: Schematic diagram representing how leiomyomas are characterized by increased CCND1 and CDK2 (mediated cell proliferation); COL1A1, COL3A1 and TGF-β3 (ECM deposition and tissue fibrosis), and DNMT1 and EZH2 (epigenetic modifiers) as well as low levels of miR-29c and miR-200c expression. Tranilast treatment significantly inhibits the expression of these genes while inducing miR-29c and miR-200c expression through repression of their promoter methylation.

In summary, these results provide support for direct effects of Tranilast on LSMC which is mediated in part through altered expression of miR-29c and miR-200c and genes functionally involved in cell cycle progression, tissue fibrosis and epigenetic regulation shown schematically in FIG. 15. Tranilast acts directly on leiomyoma cells through alteration of specific genes functionally involved in cell cycle regulation, inflammation, fibrosis, epigenetic regulation and expression of miR-29c and miR-200c. Tranilast induces miR-29c and miR-200c by suppressing methylation in miR-29c promoter and p65 binding ability in miR-200c promoter. Based on these findings Tranilast has therapeutic potential for leiomyoma treatment.

II. The Therapeutic Potential of Tranilast on Leiomyoma Initiation and or Regression in a Mouse Model A. Preparation of Mouse Model:

We injected primary leiomyoma cells under the kidney capsule of CB-17 SCID/beige mice using a 27 g needle as previously reported (Ishikawa et al., "Progesterone is essential for maintenance and growth of uterine leiomyoma," Endocrinology (2010) 151: 2433-2442; Ono et al, "Paracrine activation of WNT/beta-catenin pathway in uterine leiomyoma stem cells promotes tumor growth," Proceedings of the National Academy of Sciences of the United States of America (2013) 110: 17053-17058). After two weeks we excised the xenograft, fixed the tissue, embedded it in paraffin and obtained 5 µm sections for staining. The trichrome stain confirmed the characteristic abundance of collagens and smooth muscle cells in xenografts, indicating that the xenografts were similar in composition to leiomyomas. This animal model is used to evaluate the efficacy of Tranilast on tumor initiation, progression, histology, and expression of miR-200c and miR-29c and their respective target genes.

B. Materials & Methods:

Freshly isolated LSMC are injected under the kidney capsule of female ovariectomized CB-17 SCID/beige mice implanted with pellet containing estradiol (0.05 mg/90 d release) and progesterone (25 mg/60 d release) as previously reported (Ishikawa et al., "Progesterone is essential for maintenance and growth of uterine leiomyoma," Endocrinology (2010) 151: 2433-2442; Ono et al, "Paracrine activation of WNT/beta-catenin pathway in uterine leiomyoma stem cells promotes tumor growth," Proceedings of the National Academy of Sciences of the United States of America (2013) 110: 17053-17058). For injections of leiomyoma cells, freshly isolated cells from hysterectomy specimens are suspended in rat-tail collagen (type I) solution (BD Biosciences) at $1 \times 10^6$ cells/10 µl and grafted onto kidney capsule.

To determine the effects of Tranilast on tumor initiation, immediately after subcapsular injection of cells mice (10 per group) will be treated i.p. daily for 3 weeks with vehicle (1% DMSO) or Tranilast (50 mg/kg/day) (Kim et al., "Effects of tranilast and pentoxifylline in a mouse model of chronic asthma using house dust mite antigen," The Journal of asthma: official journal of the Association for the Care of Asthma (2009) 46: 884-894) at which point the animals are sacrificed and tumors excised, weighed and measured and subjected for further analyses detailed below.

To determine tumor progression in an additional four groups (10/group), LMSC cells are injected under the kidney capsule and tumors are allowed to develop for five weeks. Mice are then injected i.p. daily for 3 more weeks with vehicle or Tranilast (50 mg/kg/day) (Kim et al., "Effects of tranilast and pentoxifylline in a mouse model of chronic asthma using house dust mite antigen," The Journal of asthma: official journal of the Association for the Care of Asthma (2009) 46: 884-894) at which time the animals are sacrificed and tumors excised, weighed, measured and subjected for further analysis.

For tumor analysis, portions of tumors are allocated for RNA and protein extraction, and the remainder fixed in 4% neutral-buffered formalin and embedded in paraffin (FFPE) for histologic analysis. To assess the rate of collagen deposition, 5 µm cut paraffin sections are subjected to histologic analysis and stained with Masson's Trichrome and Sirius Red (Sigma-Aldrich), and images are analyzed by Image-Pro Plus software (Media Cybernetics) as described in detail in our prior publications (Khorram et al., "Nutrient restriction in utero induces remodeling of the vascular extracellular matrix in rat offspring," Reproductive sciences (2007) 14: 73-80; Khorram et al., "In utero undernutrition in rats induces increased vascular smooth muscle content in the offspring, American journal of obstetrics and gynecology (2007) 196: 486.e481-488). For Immunohistochemistry, the sections are de-paraffinized in xylene, and heated in 0.01 M citrate buffer for 15 min in a microwave oven. Slides are then incubated in methanol containing 0.3% hydrogen peroxide. Slides are incubated with primary antibody or control serum, washed, and followed by application of secondary antibody. The chromogen used is diaminobenzidine (DAKO). Sections are counterstained with hematoxylin. The area and intensity of staining is quantified using Image Pro Plus coupled to an Olympus BHS microscope/Spot RT digital camera (Olympus). After the images are calibrated for background lighting, integrated optical density (IOD) results are recorded as unweighted average optical densities per area, which is used to determine the concentration of antigen of interest. The results are expressed as percentage of IOD, which takes into account both the staining intensity and the area of staining. COL1A1 and COL3A1 will be measured by western blot and immunohistochemical analysis. Cell proliferation is assessed using the Ki-67 labeling index and PCNA staining and apoptosis is determined by TUNEL assay using ApopTag in situ apoptosis detection kit (Intergen). The remainder of tissues are frozen for mRNA (QRT-PCR) and protein (Western blot) expression analyses of miR-29c and miR-200c and their specific target genes including NF-kB (p65), DNMTs, IL8, CDK2, CCND1 and TGF-β3. Methylation specific PCR and bisulfite genomic sequencing are performed to detect the methylation status of miR-29c and miR-200c promoters. In vivo experiments with xenografts are carried out using four independent cell preparations obtained from different patients.

C. Results:

Tranilast is observed to up-regulate miR-200c and miR-29c expression and cause leiomyoma shrinkage through inhibition of NF-kB signaling, methytransferases (DNMT1), pro-inflammatory and pro-fibrotic mediators. Tranilast is observed to reduce the rate of collagen deposition (Sirius Red staining) and cell proliferation (Ki-67 and PCNA labeling index).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of increasing expression of miR-29c, miR-200c and combinations thereof in a cell, the method comprising:

contacting the cell with an amount of a tranilast active agent effective to increase expression of miR-29c, miR-200c and combinations thereof in the cell.

2. The method according to claim 1, wherein the method increases a level of two or more miRNAs in a cell.

3. The method according to claim 1, wherein the cell is in vitro.

4. The method according to claim 1, wherein the cell is in vivo.

5. The method according to claim 1, wherein the cell has been evaluated for expression of a miRNA.

6. The method according to claim 5, wherein the miRNA is selected from the group consisting of miR-29c, miR-200c and combinations thereof.

7. A method of increasing a cellular miRNA level in a subject, the method comprising:
   administering to the subject an effective amount of a tranilast active agent to increase the cellular miRNA level in the subject, wherein the cellular miRNA is selected from the group consisting of miR-29c, miR-200c and combinations thereof.

8. The method according to claim 7, wherein the method increases a level of two or more cellular miRNAs in the subject.

9. The method according to claim 7, wherein the method further comprises decreasing expression of one or more genes selected from the group consisting of: CCND1, CDK2, COL1A1, COL3A1, TGF-β3, DNMT1 and EZH2 and combinations thereof.

10. The method according to claim 7, wherein the method is a method of treating the subject for a leiomyoma.

11. The method according to claim 10, wherein the leiomyoma comprises a uterine leiomyoma.

12. The method according to claim 11, wherein the subject has been diagnosed as having at least one of down regulated miR-29c and miR-200c.

13. The method according to claim 12, wherein the method further comprises diagnosing the subject as having at least one of down regulated miR-29 c and miR-200c.

* * * * *

UNITED STATES PATENT AND TRADEMARK OFFICE
CERTIFICATE OF CORRECTION

PATENT NO. : 10,517,842 B2  
APPLICATION NO. : 15/921380  
DATED : December 31, 2019  
INVENTOR(S) : Omid Khorram et al.

Page 1 of 1

It is certified that error appears in the above-identified patent and that said Letters Patent is hereby corrected as shown below:

In the Specification

Insert the Government Support Clause at Column 1, Line 14, so the paragraph reads as follows:
-- GOVERNMENT RIGHTS
This Invention was made with government support under grant R21 HD088868-02 awarded by the National Institutes of Health. The government has certain rights in the invention. --

Signed and Sealed this  
Twenty-ninth Day of December, 2020

Andrei Iancu  
*Director of the United States Patent and Trademark Office*

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 1
gccctctgtg ccacagatgt                                                   20

<210> SEQ ID NO 2
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 2
ccccgctgcc accat                                                        15

<210> SEQ ID NO 3
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 3
ttcccctcat caagagctat ctgt                                              24

<210> SEQ ID NO 4
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 4
acccgatgag aatggcagaa                                                   20

<210> SEQ ID NO 5
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 5
ccaatggtgc tcctggtatt                                                   20
```

```
<210> SEQ ID NO 6
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 6
gttcaccgct gttaccctt                                                  19

<210> SEQ ID NO 7
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 7
attattttgg cacaacagga agct                                            24

<210> SEQ ID NO 8
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 8
tccgcatagg actgaccaag at                                              22

<210> SEQ ID NO 9
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 9
cgggctttgg acaccaatta                                                 20

<210> SEQ ID NO 10
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 10
gggcgcacac agcagttc                                                   18

<210> SEQ ID NO 11
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 11
gaaccaacgg agaaaaaaat gg                                              22

<210> SEQ ID NO 12
<211> LENGTH: 18
<212> TYPE: DNA
<213> ORGANISM: Artificial sequence
<220> FEATURE:
<223> OTHER INFORMATION: synthetic polynucleotide
```

<400> SEQUENCE: 12
gggagggtgg gtcttgga					18

<210> SEQ ID NO 13
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 13
ggaggatcac cgagatgata aag					23

<210> SEQ ID NO 14
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 14
ttctgctgtg cccttatctg					20

<210> SEQ ID NO 15
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 15
cgagccgcct ggatacc					17

<210> SEQ ID NO 16
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 16
cagttccgaa aaccaacaaa ataga					25

<210> SEQ ID NO 17
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 17
gatgggatta aattttggaa tattc					25

<210> SEQ ID NO 18
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 18
aaatcctaaa acccgtcgaa					20

<210> SEQ ID NO 19
<211> LENGTH: 24

```
<212> TYPE: DNA
<213> ORGANISM: Artificial sequence
<220> FEATURE:
<223> OTHER INFORMATION: synthetic polynucleotide

<400> SEQUENCE: 19
gggattaaat tttggaatat ttgg                                  24

<210> SEQ ID NO 20
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 20
atcaaatcct aaaacccatc aaa                                   23

<210> SEQ ID NO 21
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 21
gaatttgggg ttttaaagtt ttttc                                 25

<210> SEQ ID NO 22
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 22
caccctaaat cgctaatcac g                                     21

<210> SEQ ID NO 23
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 23
gaatttgggg ttttaaagtt ttttt                                 25

<210> SEQ ID NO 24
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 24
cacaccctaa atcactaatc acaaa                                 25
```